(12) United States Patent
Fike et al.

(10) Patent No.: US 10,669,522 B2
(45) Date of Patent: Jun. 2, 2020

(54) COMPOSITIONS AND METHODS FOR STABILIZING SUSCEPTIBLE COMPOUNDS

(75) Inventors: Richard Fike, Clarence, NY (US); Bruce Branchaud, Eugene, OR (US); Shawn Barrett, Clarence Center, NY (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 159 days.

(21) Appl. No.: 13/984,263

(22) PCT Filed: Feb. 7, 2012

(86) PCT No.: PCT/US2012/024194
§ 371 (c)(1),
(2), (4) Date: Aug. 7, 2013

(87) PCT Pub. No.: WO2012/109279
PCT Pub. Date: Aug. 16, 2012

(65) Prior Publication Data
US 2013/0316004 A1 Nov. 28, 2013

Related U.S. Application Data

(60) Provisional application No. 61/440,237, filed on Feb. 7, 2011.

(51) Int. Cl.
*C12N 5/00* (2006.01)
(52) U.S. Cl.
CPC ........ *C12N 5/0018* (2013.01); *C12N 2500/34* (2013.01); *C12N 2500/46* (2013.01)
(58) Field of Classification Search
None
See application file for complete search history.

(56) References Cited

U.S. PATENT DOCUMENTS

| 4,409,331 | A | | 10/1983 | Lim | |
|---|---|---|---|---|---|
| 5,766,626 | A | * | 6/1998 | Gross | A61K 9/1271 424/450 |
| 5,817,343 | A | * | 10/1998 | Burke | A61K 9/0024 424/426 |
| 2007/0041934 | A1 | * | 2/2007 | William | C08G 73/0206 424/78.3 |
| 2008/0026108 | A1 | * | 1/2008 | Subramanian | A23K 40/30 426/72 |

FOREIGN PATENT DOCUMENTS

| CN | 1798543 | | 7/2006 | |
|---|---|---|---|---|
| EP | 0276575 | | 8/1988 | |
| EP | 0429082 | | 5/1991 | |
| EP | 1702675 | | 9/2006 | |
| JP | 62-32824 | | 2/1987 | |
| JP | 2002505671 | A | 2/2002 | |
| WO | WO 8901034 | A1 * | 2/1989 | ........... A61K 9/1652 |
| WO | WO-91/02071 | | 2/1991 | |
| WO | 1993/16687 | | 9/1993 | |
| WO | WO-98/24883 | | 6/1998 | |
| WO | WO-1998/56426 | | 12/1998 | |
| WO | WO-03048313 | A2 | 6/2003 | |
| WO | 2003/055906 | | 7/2003 | |
| WO | 2006/045438 | | 5/2006 | |
| WO | WO-2009/011663 | | 1/2009 | |
| WO | WO-2009/042945 | | 4/2009 | |
| WO | WO-2009/112682 | | 9/2009 | |
| WO | WO-2009/144569 | | 12/2009 | |
| WO | WO-2013/096858 | | 6/2013 | |

OTHER PUBLICATIONS

Kano-Sueoka, T. et al., "Effects of Phosphoethanolamine and Ethanolamine on Growth of Mammary Carcinoma Cells in Culture", Exp. Cell Research, vol. 136 (1), Nov. 1, 1981, 137-145.*
Maziere, C. et al., "Effect of Manipulation of Phospholipid Polar Head Group on Low Density Lipoprotein Metabolism in Human Cultured Fibroblasts", Biochemical and Biophysical Research, vol. 137 (1), May 29, 1986, 43-49.*
Kurano, S. et al., "Utilization and Stability of Vitamins in Serum-Containing and serum-free media in CHO cell culture", *Cytotechnology*,. vol. 4 (3), Jan. 1, 1990, 243-250.
Murakami, H. et al., "Growth of Hybridoma Cells in Serum-Free Medium: Ethanoloamine is an Essential Component", *Proc. Natl. Acad, Sci.*, vol. 79 (4), Feb. 1982, 1158-1162.
PCT/US2012/024194, "International Search Report and Written Opinion dated Aug. 21, 2012", Aug. 21, 2012, 1-21.
Cleland, J. et al., "Stable Formulations of Recombinant Human Growth Hormone and Interferon-γ for Microencapsulation in Biodegradable Microspheres", *Pharmaceutical Research*, vol. 13 (10), Jan. 1, 1996, 1464-1475.
EP14161140, "European Search Report dated Dec. 23, 2014", 6 Pages.
Lu, T et al., "Comparison of the biological stability of liposome-encapsulated nerve growth factor at different depot stages", *Chinese Journal of Clinical Rehabilitation*, vol. 9 (29), Aug. 7, 2005, 214-217.
Alpert, A. et al., "Hydrophilic-Interaction Chromatography for the Separation of Peptides, Nucleic Acids and Other Polar Compounds", *Journal of Chromatography*, vol. 499, Jan. 19, 1990, 177-196.

(Continued)

*Primary Examiner* — Nghi V Nguyen

(57) ABSTRACT

Methods for increasing the stability of, or protecting, labile components, such as ethanolamine, growth factors, vitamins, etc., in compositions such as a cell culture medium, are described. Stability of the labile compound is increased either, by derivatization or by sequestering the labile compound. Sequestering can be done either by encapsulation within a microcapsule or by the use of sequestering agents. Encapsulation can provide controlled release of the susceptible compound being protected. These methods may improve or extend the storage conditions, the shipping and handling of media compositions comprising the labile compounds at room temperature rather than at lower temperatures, thereby decreasing shipping costs.

19 Claims, 16 Drawing Sheets

(56) References Cited

OTHER PUBLICATIONS

Annan, N. T. et al., "Encapsulation in alginate-coated gelatin microspheres improves survival of the probiotic Bifidobacterium adolescentis 15703T during exposure to simulated gastro-intestinal conditions", *Food Research International*, vol. 41 (2), Nov. 17, 2007, 184-193.

Burgain, J. et al., "Encapsulation of probiotic living cells: From laboratory scale to industrial applications", *Journal of Food Engineering*, vol. 104 (4), Jan. 5, 2011, 467-483.

Churms, S., "Recent progress in carbohydrate separation by high performance liquid chromatography based on hydrophilic", *Journal of Chromatography*, vol. 720, Jan. 12, 1996, 75-91.

Gibbs, B. et al., "Encapsulation in the Food industry: a review", *International Journal of Food Sciences and Nutrition*, vol. 50 (3), 1999, 213-224.

Kehoe, D. et al., "Scalable Stirred-Suspension Bioreactor Culture of Human Pluripotent Stem Cells", *Tissue Engineering: Part A*, vol. 16(2), Jan. 1, 2010, pp. 405-421.

Maysinger, D. et al., "Microencapsulated Ciliary Neurotrophic Factor: Physical Properties and Biological Activities", *Experimental Neurology*, vol. 138 (2), Jan. 4, 1996, 177-188.

Righetto, A. et al., "Vitamin C stability in encapsulated green West Indian cherry juice and in encapsulated synthetic ascorbic acid", *Journal of the Science of Food and Agriculture*, vol. 86 (1), Jun. 1, 2006, 1202-1208.

Sideratou, Z. et al., "Arginine end-functionalized poly(L-lysine) dendrigrafts for the stabilization and controlled release of insulin", *Journal of Colloid .and Interface Science*, vol. 351, Aug. 4, 2010, 433-441.

Wijagkanalan, W. et al., "Designing Dendrimers for Drug Delivery and Imaging: Pharmacokinetic Considerations", *Pharm Res*, vol. 28 (7), Dec. 23, 2011, 1500-1519.

Bielinska, A. et al., "Application of membrane-based dendrimer/DNA complexes for solid phase transfection in vitro and in vivo", *Biomaterials*, vol. 21, May 2000, 877-888.

Liu, H et al., "Research Progress in the Application of Dendrimers" *Polymer Bulletin*, Department of Polymer Materials, Dalian University of Technology, Dalian 116012, Jun. 2005, 13 pages.

EP16202748.6, , "European Search Report", dated Jun. 19, 2017, 9 Pages.

EP16202748.6, , "Partial European Search Report", dated Mar. 10, 2017, 8 Pages.

Gonnet, M. et al., "New trends in encapsulation of lipsoluble vitamins", *Journal of Controlled Release*, vol. 146, No. 3, Jun. 25, 2010, 276-290.

O'Regan, J. et al., "Sodium caseinate-maltodextrin conjugate stabilized double emulsions: Encapsulation and stability", *Food Research International*, vol. 43, No. 1, 2010, 224-231.

Romo-Hualde, A. et al., "Supercritical fluid extraction and microencapsulation of bioactive compounds from red peppers (*Capsicum annum* L.) by-products", *Food Chemistry* vol. 133, No. 3, Jan. 27, 2012, 1045-1049.

Tian-Run, L. et al., "Comparison of the biological stability of liposome-encapsulated nerve growth factor at different depot stages", *Chinese Journal of Clinical Rehabilitation*, vol. 9, No. 29, Aug. 7, 2005, 214-216.

Wegmuller, R. et al., "Development, Stability, and Sensory Testing of Microcapsules Containing Iron, Iodine, and Vitamin A for Use in Food Fortification" *Journal of Food Science*, vol. 71, No. 2, Jan. 27, 2012, S181-S187.

\* cited by examiner

NAE

| concentration (mg/mL) | peak area | sample run |
|---|---|---|
| 19.49 | 708.98 | DANA_102110_04 |
| 0.001949 | 0 | DANA_102110_05 |
| 0.00001949 | 0 | DANA_102110_06 |
| 0.1949 | 39.69 | DANA_102110_07 |
| 1.949 | 197.25 | DANA_102110_08 |
| 19.49 | 686.52 | DANA_102110_09 |
| 0.001949 | 0 | DANA_102210_01 |
| 0.00001949 | 0 | DANA_102210_02 |
| 0.01949 | 7.91 | DANA_102210_03 |
| 0.1949 | 45.46 | DANA_102210_04 |
| 1.949 | 210.05 | DANA_102210_05 |
| 19.49 | 702.28 | DANA_102210_06 |
| 0.01949 | 9.74 | DANA_102210_07 |
| 0.1949 | 40.06 | DANA_102210_08 |
| 1.949 | 208.93 | DANA_102210_09 |
| 0.1949 | 40.09 | DANA_102210_11 |
| 0.01949 | 8.79 | DANA_102210_10 |

Needle and syringe:

Alginate solution containing target molecule(s)

Syringe with 26g or 30g needle

Calcium chloride bath (ionic cross-linker of polyguluronate carboxylates)

Drying step (~2.6mm) (~0.95mm)

Spray mist:

Calcium chloride bath (ionic cross-linker of polyguluronate carboxylates)

Alginate solution containing target molecule(s) in aerosol spray

Drying step (~1mm) (~0.43mm)

FIGURE 3A g/L CaCl$_2$

| % alginate | 13.32 | 6.66 | 3.33 |
|---|---|---|---|
| 2 | Refractile, spherical | Refractile, spherical | Refractile, spherical |
| 1 | Refractile, spherical | Flattened disc, not spherical | Flattened disc, not spherical |
| 0.5 | Flattened disc, not spherical | Flattened disc, not spherical | Flattened disc, not spherical |

|  | Bead Count | | OD$_{550}$ | |
|---|---|---|---|---|
|  | mean | SD | mean | SD |
| No Ship (n=12) | 72.83 | 10.13 | 0.030 | 0.0042 |
| Shipped (n=11) | 76.36 | 10.16 | 0.031 | 0.0045 |

FIGURE 3B

| Ethanol. (g/ml alginate) | Conc. | Bead Characteristics | Size (mm) |
|---|---|---|---|
| 0.0135 | 1000x | Dry, hard, separates well | 0.945 |
| 0.0675 | 5000x | Dry, hard, separates well | 1.33 |
| 0.1350 | 10,000x | Dry, hard, separates well | 1.86 |
| 0.3375 | 25,000x | Mostly dry, hard, but shiny | 2.17 |
| 0.6750 | 50,000x | Mostly dry, but beads sticky | 2.44 |

Time to complete B12 release from 3% alginate with PLL

| | 15 min. | 30 min. | 45 min. | 60 min. | 90 min. |
|---|---|---|---|---|---|
| Standard | B12 remaining throughout bead | B12 remaining at core | B12 remaining at core | B12 remaining at core: (slight) | B12 release complete |
| Reduced | B12 remaining throughout bead | B12 remaining at core | B12 remaining at core: (faint) | B12 release complete | ---------- |
| Spray | B12 release complete | ---------- | ---------- | ---------- | ---------- |

FIGURE 3C

COMPOSITIONS AND METHODS FOR STABILIZING SUSCEPTIBLE COMPOUNDS

CROSS-REFERENCE TO RELATED APPLICATIONS

This application is a national phase filing of PCT/US12/24194 filed Feb. 7, 2012, which claims the benefit of U.S. Provisional Application No. 61/440,237, filed Feb. 7, 2011, under 35 U.S.C. § 119(e), whose disclosures are incorporated by reference in their entirety.

Some chemicals are known to degrade over time, even when they are in dry formulations, either in the presence of moisture, or due to gradual interaction with other components within the formulation. This is commonly seen in the pharmaceutical industry, food industry, and even in the cell culture media industry and it contributes to shorter shelf-life of the product. For instance, ethanolamine, is a susceptible compound in cell culture media and degrades over time, contributing to shorter shelf-life of the cell culture media. Ethanolamine, also known as 2-amino ethanol or monoethanolamine, is an alkanolamine characterized by the presence of both an amine group and a hydroxyl group and has the following chemical structure:

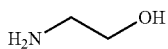

Ethanolamine is commonly used in the chemical industry as a component in detergents, pharmaceuticals, and cosmetics. For example, it is used in both water-based and solvent-based coatings to enhance the solubility, reducibility, pigment dispersing, and pH stability. Ethanolamine is also used in the water treatment industry, and more particularly in the steam cycles of power plants, to prevent corrosion of metal components. It is also used to scrub or remove acidic components, such as hydrogen sulfide and carbon dioxide from gas streams in natural and refinery gas operations. Ethanolamine is produced by the reaction of ethylene oxide with ammonia, along with the additional secondary products of diethanolamine and triethanolamine.

Cell culture media provide the nutrients necessary to maintain and grow cells in a controlled, artificial and in vitro environment. Media formulations have been used to cultivate a number of cell types including bacterial cells, and eukaryotic cells such as animal, plants, etc. Ethanolamine is a useful component of eukaryotic cell culture media and is generally supplemented later as it is a susceptible component. Ethanolamine can be problematic in certain compositions because of its low stability. For example, in cell culture media, in the presence of amino acids, ethanolamine degrades rapidly. This instability increases in a warmer environments, such as that encountered during the process of preparing dry powder cell culture media, resulting in ethanolamine degradation and reduced shelf life of the cell culture media. Similarly, a number of cell culture components such as vitamins, growth factors like insulin, and cytokines, etc., may also be unstable in media formulations, especially in single component dry-format media formulations, which may contain from 60-100 different chemicals of varied reactivities, including amino acids.

There exists a need for stabilizing and/or protecting labile components present in cell culture media formulations, especially in single component cell culture media formulations, in dry-format media formulations, etc.

SUMMARY

The present disclosure provides methods for increasing or protecting the stability of a labile compound or component, a sensitive or susceptible component or compound, (terms which may be used interchangeably), in a composition, including but not limited to, a cell culture medium, a cell culture supplement, pharmaceuticals, nutraceuticals, food supplements, vitamin enriched formulations, cosmetics, detergents, etc.

Thus, in one embodiment, the disclosure is directed to composition, like a cell culture composition, comprising a protected labile molecule, wherein the protected labile molecule is prevented from adverse reactions with a cell culture component in the cell culture composition. In certain embodiments, the cell culture composition may be a dry-format cell culture powder whereas in other, it may be a liquid cell culture medium. In a further embodiment, the protected labile molecule may be selected from any labile molecule in a group consisting of molecules like ethanolamine, a growth factor, a vitamin, a cytokine, etc. In some embodiments, the labile molecule may be protected by derivatization of the labile molecule or by sequestration of the labile molecule. In one aspect of this embodiment, the labile molecule is ethanolamine. In another aspect of this embodiment, the protected labile molecule may be a growth factor like insulin, or a vitamin like B12, or thiamine, etc.

By a 'labile molecule, component or compound', or 'a susceptible molecule, component or compound' is meant, one that is prone to degradation or an unwanted interaction with other components in the same composition, for e.g., polyamines like ethanolamine, vitamins, growth factors, etc. in compositions such as culture media, supplements, pharmaceuticals, nutraceuticals, food supplements, vitamin enriched formulations, cosmetics, detergents, etc., where these components degrade quickly or over periods of time during storage due to unwanted interactions with other chemicals within the same composition.

In a further aspect of the above embodiment, the cell culture composition comprises a protected labile molecule wherein the protected labile molecule demonstrates enhanced stability in the cell culture composition, and wherein the labile molecule is ethanolamine. In a further embodiment, the cell culture composition may be a dry-format cell culture powder or a liquid cell culture medium.

In a preferred embodiment, the ethanolamine is protected by either derivatization or by sequestration. The derivatization may be by reaction with a sugar alcohol, or an amino sugar, or an uronic acid, or a phosphorylated sugar.

In a further embodiment, the sugar alcohol may be selected from the group consisting of allitol, altritol, fructitol, galactitol, glucitol, gulitol, iditol, mannitol, sorbitol, talitol, tagatitol, arabinitol, ribitol, ribulitol, xylitol, xylulitol, lyxitol, erythrulitol, erythritol, and threitol.

In yet another embodiment, the amino sugar may be selected from the group consisting of allosamine, altrosamine, fructosamine, galactosamine, glucosamine, gulosamine, idosamine, mannosamine, sorbosamine, talosamine, tagatosamine, arabinosamine, ribosamine, ribulosamine, xylosamine, xylulosamine, lyxosamine, erythrulosamine, erythrosamine, and threosamine.

In another embodiment, the uronic acid may be selected from the group consisting of alluronic acid, altruronic acid, fructuronic acid, galacturonic acid, glucuronic acid, guluronic acid, iduronic acid, mannuronic acid, sorburonic acid, taluronic acid, tagaturonic acid, arabinuronic acid, riburonic acid, ribuluronic acid, xyluronic acid, xyluluronic acid, lyxuronic acid, erythruluronic acid, erythruronic acid, and threuronic acid.

In yet another embodiment, the phosphorylated sugar is selected from the group consisting of glyceraldehyde 3-phosphate and dihydroxyacetone phosphate.

In one aspect, the sequestration of the labile molecule, for e.g., ethanolamine, may be done by encapsulation of the labile molecule within a soluble matrix, or by encapsulation of the labile molecule within an insoluble matrix. In a preferred embodiment, the labile molecule to be encapsulated is ethanolamine. In other embodiments, the labile components to be encapsulated are vitamins, growth factors, cytokines, etc.

In another aspect, the labile molecule is complexed with a dendrimer before encapsulation. In other aspects, the labile molecule directly encapsulated without being complexed with a dendrimer.

In one aspect, the soluble matrix or the insoluble matrix for encapsulation may be further coated with a protective coating. In a further aspect, the protective coating may be made up of poly-L-lysine or polyornithine.

In one embodiment, the insoluble matrix may be selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, poly-glycolic acid, PLGA (poly-lactic-co-glycolic acid), collagen, polyhydroxyalkanoates (PHA), poly-ε-caprolactone, poly-ortho esters, poly-anhydrides, poly-phosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone and carrageenan. In a further embodiment, the microencapsulation may be done with a scaffolding matrices that includes, but is not limited to, poly-glycolic acid, PLGA (poly-lactic-co-glycolic acid), collagen, polyhydroxyalkanoates (PHA), poly-ε-caprolactone, poly-ortho esters, poly-anhydrides, poly-phosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, etc.

In another embodiment, the soluble matrix may be a molecule comprising an alcohol, a ketone or an aldehyde. In a further embodiment, the soluble matrix may be a hexose sugar selected from the group consisting of glucose, mannose, fructose, maltodextrin and galactose. In a preferred aspect, the hexose sugar may be maltodextrin.

In one aspect, the ethanolamine derivative has the following formula:

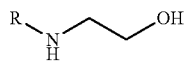

wherein R is an acetyl group or an amino acid. In a preferred embodiment, the ethanolamine derivative is N-acetylethanolamine (NAE).

In certain embodiment, the compositions described in this disclosure may be selected from the group consisting of a cell culture medium, a cell culture supplement, a feed and a cell culture media concentrate.

In another aspect, the disclosure describes a method of making a cell culture composition comprising one or more protected labile molecules, further comprising: a) derivatizing and/or sequestering the one or more labile molecules to produce the one or more protected labile molecules; b) admixing the one or more protected labile molecules with one or more cell culture components to make the cell culture composition, wherein the one or more protected labile molecules are prevented from adverse reactions with one or more cell culture components compared to an unprotected labile molecule, wherein at least one of the protected labile molecules is ethanolamine.

In a certain embodiment, the derivatization of the labile molecule may be with a sugar alcohol, or an amino sugar, or a uronic acid, or a phosphorylated sugar.

In one aspect, the sugar alcohol may be selected from the group consisting of allitol, altritol, fructitol, galactitol, glucitol, gulitol, iditol, mannitol, sorbitol, talitol, tagatitol, arabinitol, ribitol, ribulitol, xylitol, xylulitol, lyxitol, erythrulitol, erythritol, and threitol. In another aspect, the amino sugar may be selected from the group consisting of allosamine, altrosamine, fructosamine, galactosamine, glucosamine, gulosamine, idosamine, mannosamine, sorbosamine, talosamine, tagatosamine, arabinosamine, ribosamine, ribulosamine, xylosamine, xylulosamine, lyxosamine, erythrulosamine, erythrosamine, and threosamine. In a third aspect, the uronic acid may be selected from the group consisting of alluronic acid, altruronic acid, fructuronic acid, galacturonic acid, glucuronic acid, guluronic acid, iduronic acid, mannuronic acid, sorburonic acid, taluronic acid, tagaturonic acid, arabinuronic acid, riburonic acid, ribuluronic acid, xyluronic acid, xyluluronic acid, lyxuronic acid, erythruluronic acid, erythruronic acid, and threuronic acid. In a fourth aspect, the phosphorylated sugar is selected from the group consisting of glyceraldehyde 3-phosphate and dihydroxyacetone phosphate.

In one embodiment, the sequestering of the labile molecule may be done by encapsulation within a soluble matrix, or by encapsulation of the labile molecule within an insoluble matrix. In one aspect, the soluble matrix or the insoluble matrix may be further coated with a protective coating while in another aspect, the soluble matrix or the insoluble matrix may not be further coated with a protective coating. In a further aspect, the protective coating is made up of poly-L-lysine or polyornithine.

In another aspect, the soluble matrix is made up of a molecule comprising an alcohol, a ketone or an aldehyde, which may be a sugar such as maltodextrin.

In yet another aspect, the insoluble matrix may be selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, poly-glycolic acid, PLGA (poly-lactic-co-glycolic acid), collagen, polyhydroxyalkanoates (PHA), poly-ε-caprolactone, poly-ortho esters, poly-anhydrides, poly-phosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone and carrageenan.

In one embodiment, the disclosure provides a method of encapsulating or microencapsulating (used interchangeably) a labile compound for protection from adverse reactions within a composition, comprising: a) optionally, reacting the labile compound with a dendrimer to produce a dendrimer-labile compound complex; b) encapsulating the dendrimer-labile compound complex of step a), or, the labile compound within a sequestering agent, to produce an encapsulated dendrimer-labile compound complex, or an encapsulated labile compound; and c) admixing the encapsulated dendrimer-labile compound complex or the encapsulated labile compound of step c) with one or more components in the composition. The labile compound may be selected from the group consisting of ethanolamine, a growth factor, a vitamin and a cytokine.

In a further aspect, the method of microencapsulation or encapsulation composition may be used to prepare a cell culture medium, a cell culture supplement, or a cell culture feed, any of which may be in a dry media format. In a preferred embodiment, the dry media is an agglomerated media. In various aspects, the method would use media that comprised labile molecules or compounds obtained by the sequestering of the labile molecule by encapsulation within a soluble matrix, or within an insoluble matrix. In one aspect of the method, the soluble matrix or the insoluble matrix may be further coated with a protective coating while in another aspect, the soluble matrix or the insoluble matrix may not be further coated with a protective coating. In a further aspect of the method, the protective coating is made up of poly-L-lysine or polyornithine. In another aspect of the method, the soluble matrix may be made up of a molecule comprising an alcohol, a ketone or an aldehyde, which may be a sugar such as maltodextrin.

In some embodiments of the method, the insoluble matrix may be selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, poly-glycolic acid, PLGA (poly-lactic-co-glycolic acid), collagen, poly-hydroxyalkanoates (PHA), poly-ε-caprolactone, poly-ortho esters, poly-anhydrides, poly-phosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone and carrageenan.

In other embodiments of the method, the dendrimer used to complex with the labile compound may be selected from the group consisting of a polyamidoamine (PAMAM) dendrimer, a polypropyleneimine (PPI) dendrimer, a phosphorylated dendrimer, a polylysine dendrimer, a polyethylenimine dendrimer, an iptycene dendrimer, an aliphatic poly(ether) dendrimer, an aromatic polyether dendrimer, and a polypropylamine (POPAM) dendrimer.

In certain aspects, the disclosure is directed to the use of the compositions described above, for the preparation of a cell culture medium, a cell culture supplement, or a cell culture feed. In one aspect, the cell culture supplement, or the cell culture feed is used for the culture of a cell under suitable conditions. The cell may be a mammalian cell, a recombinant cells, a recombinant, mammalian cell that produces a desired product. In a preferred embodiment, the cell is a Chinese Hamster Ovary (CHO) cell, and in a further aspect, the CHO cell expresses a recombinant protein of interest, or of commercial value.

In a another embodiment, the present disclosure provides methods for increasing the stability of labile components, either by derivatizing the labile component to a stable form, or by sequestering the labile component by methods including but not limited to, encapsulation. Thus, the present disclosure provides methods for increasing the stability of, for e.g., a dry-format media which labile components like ethanolamine, vitamins, growth factors, etc. at room temperature rather than at lower temperatures, for extended periods of time. The present disclosure provides methods for increasing the stability of, for e.g., a dry-format medium comprising labile components like ethanolamine, vitamins, growth factors, etc. which can be transported at ambient temperatures or room temperature, without the need for dry ice, or without refrigeration. The present disclosure provides compositions comprising the stabilized equivalents of a degradation-susceptible compound, for e.g., compositions comprising stabilized polyamines, or stabilized vitamins, etc. The composition may be in any form, including in a semi-solid paste, semi-dry, or in dry formats. Media and media supplement in dry formulations or dry format media may be in any of the following: dry powder media (DPM), agglomerated dry format (AGT) or advanced powder media (APM). The cell culture medium may be a dry-format cell culture medium or a liquid medium. Additionally, the cell culture medium may be one single component medium, or may have more than one component, for example, a two or a three component medium. The dry-format medium may be a single component medium formulation, or a multiple component medium formulation, that may e reconstituted with solvent to generate a cell culture medium that is ready for cell culture cultivation. In some embodiments, the reconstituted formulation may be pre-auto-pH and pre-auto-osmolality adjusted. By this is meant, no further acid/base or osmolality adjusting components need to be added to the medium during the process of reconstitution with solvent, thereby making reconstitution a simple step for the end-user.

The disclosure is also directed to stabilizing ethanolamine or other labile components in any application, including but not limited to, cell culture media, any chemical composition comprising a labile molecule such as ethanolamine used in the pharmaceutical industry, cosmetic industry, enzyme industry, buffers as in the food industry, in industrial applications such as cleaning agents, in methods of treating water (to control corrosion), paint industry, in detergents, removing acids from a gas, etc. The methods and compositions disclosed here can be used in any field for protecting degradation-prone compounds, and the skilled artisan may adapt the methods for stabilizing labile components described in this disclosure to any other application. While microencapsulation of compounds is known in the art, the current disclosure provides novel methods of encapsulating a dendrimer-labile component complex, wherein a dendrimer includes but is not limited to, polyamidoamine dendrimer, a polypropyleneimine dendrimer, or a polypropylamine (POPAM) dendrimer, etc. In this method, a dendrimer forms a complex with a sensitive compound like ethanolamine or insulin, etc., and then, the dendrimer-compound complex is encapsulated. The encapsulated dendrimer-labile compound complex is used for the preparation of stabilized compositions like cell culture media. Thus, the present disclosure provides methods of making improved compositions like cell culture media which comprise encapsulated, dendrimer-labile compound complexes, which improve cell culture media storage, transportation of the medium at ambient temperatures, and may allow for the controlled release of the labile component from the encapsulated complex over long periods of time.

Using the methods described in this disclosure, such as derivatizing the labile compound, and/or, sequestering (as in encapsulation, and/or labile molecule-dendrimer encapsulation), the labile compound can be protected and/or stabilized in any composition, such as cell culture media for instance. Therefore, using the methods of the present disclosure, the protected compounds may be more stable by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% than a comparable unprotected or labile molecule in a similar composition. Measurements of percent (%) stability can be measured or inferred by many methods; for e.g., by the ability of a protected/unprotected molecule (protected ethanolamine vs. unprotected ethanolamine) to allow cell growth as measure by viable cell density of a cell culture, or a measure of a modified compound like a modified ethanolamine in a composition using LCMS spectrometry, or by measuring the % degradation of ethanolamine in a composition, etc. Stability may also be considered as enhanced if the protected molecule can withstand destructive factors such as increased or decreased temperatures, exposure to radiation (e.g., UV, sunlight, etc.), exposure to humidity, wetness, extreme dryness, mechanical disruption (during transport), etc. as compared to an unprotected molecule exposed to similar conditions. Stability may also be expressed as 1.5×, 2×, 3×, 4×, 5×, 6×, 7×, 10×, 15×, 20×, 25×, 3×, 35×, 40×, 4×, 50×, 55×, 60×, 65×, 70×, 75×, up to 100× more stable than an unprotected molecule exposed to similar conditions, in any one or more of the comparative assays (viable cell density of a cell culture, or a measure of a modified compound like a modified molecule in a composition using LCMS spectrometry, or by measuring the % degradation) described above.

In one aspect of the disclosure, stability of the susceptible compound is increased by forming an amide bond at the amino moiety of the compound, for e.g., acetylating the compound at the amino group. For instance, ethanolamine stability is increased by using an acetyl derivative, a covalent linkage at the ethanolamine amine group. In one embodiment, the covalent linkage is an amide bond. The ethanolamine derivative may have the following formula:

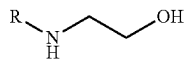

wherein R is an acetyl group or an amino acid.

In one aspect, stability of the susceptible compound may be increased by using a sequestering agent to protect the susceptible compound. This process may be referred to, interchangeably, as encapsulation or embedding. A sequestering agent can be any agent that 'protects' or 'separates' or 'encapsulates' or 'embeds' the susceptible compound away from any element or compound that gradually degrades it. For e.g., ethanolamine may be stabilized by encapsulating the ethanolamine within a sequestering agent that protects the ethanolamine from adverse reactions. The sequestering agent may be a soluble encapsulating matrix or an insoluble encapsulating matrix.

In one embodiment, the sequestering agent may be a soluble encapsulating matrix, such as a ketone-containing compound, or an aldehyde-containing compound, including, but not limited to, a sugar (e.g., glucose), or a derivative thereof, or a keto acid. For instance, the sequestering agent may be a soluble, crystalline matrix made up of sugars like maltodextrin, etc. which can dissolve in an aqueous based medium upon reconstitution.

In another embodiment, the encapsulating matrix may be an insoluble matrix, for example, alginate, etc., which may encapsulate the labile compound. The insoluble matrix or beads readily release the encapsulated labile material into solution upon reconstitution with solvents like water or buffer, and can be separated out for the reconstituted media, via filtration for instance. Examples of insoluble matrix encapsulating agents include, but are not limited to, alginate, chitosan, PEG matrix, ploy-lactic co-glycolic acid (PLGA), gelatin and its derivatives, collagen and its derivatives, polyethylene terephthalate (PET), permselective materials, membranes, resins, gums, arabinogalactan, maltodextrins, other oligo- or polysaccharide matrices, lipids, waxes, paraffins, oils, etc. In a further embodiment, the encapsulating matrix such as alginate, may encapsulate a complex of a labile compound with a dendrimeric compound. In the labile compound-dendrimer complex, the dendrimer forms a scaffold around the degradation-prone, labile substance. The further encapsulation of the labile compound-dendrimer complex with a soluble/an insoluble matrix, provides an additional layer of protection. In addition, the dendrimer-labile compound complex can result in the slow release of the labile compound upon reconstitution with solvent, which may be desired in certain instances.

Formation of capsules or beads: Alginate is a crosslinked hydrogel, which is dissolved with say, ethanolamine (or any susceptible substance) and then this resulting solution is dropped into a calcium solution to form capsules (needle syringe method). An alternate method for forming beads is by the spray-mist method. The beads are collected, washed to remove excess calcium and dried. Alginate when dried forms a hard, refractile bead that can be mixed with dry powder media such as DPM, APM or AGT, and the ethanolamine is protected. In one embodiment, alginate used for encapsulating ethanolamine is formed into beads either by the needle syringe method or in another, by the spray mist method. Spray mist method results in smaller beads. When dendrimers containing ethanolamine are similarly encapsulated in alginate, and the media is reconstituted with solvent, alginate and the dendrimers readily release the encapsulated material into solution. The capsules can be filtered off from the medium.

In one aspect, the composition with increased ethanolamine stability is a cosmetic or a pharmaceutical. In one embodiment, the cosmetic or pharmaceutical composition is a powdered composition. In another embodiment, the cosmetic or pharmaceutical composition is a solution.

In another aspect, the composition with increased ethanolamine stability is a cell culture medium. In one embodiment, the cell culture medium is a powdered cell culture medium. In another embodiment, the cell culture medium is a solution. This aspect includes a method of increasing the stability of ethanolamine in a powdered or liquid cell culture medium, as well as powdered or liquid cell culture medium produced by such methods.

One embodiment is directed to a method of increasing ethanolamine stability in a powdered cell culture medium, the method comprising combining an ethanolamine derivative or ethanolamine that has been complexed with a sequestering agent ("sequestered ethanolamine") with a powdered cell culture medium comprising one or more amino acids, wherein the powdered cell culture medium comprising one or more amino acids and the ethanolamine derivative or the sequestered ethanolamine exhibits increased ethanolamine stability. In certain embodiments, the method further comprises before the combining step, a step of complexing ethanolamine with the sequestering agent to produce the sequestered ethanolamine.

In another aspect, this disclosure provides a method of preparing an aqueous cell culture medium by combining an aqueous cell culture medium with an ethanolamine derivative or ethanolamine that has been complexed with a sequestering agent ("sequestered ethanolamine"). In one embodiment, the method of preparing an aqueous cell culture medium comprises combining an ethanolamine derivative or ethanolamine that has been complexed with a sequestering agent ("sequestered ethanolamine") with a cell culture medium solution comprising one or more amino acids. The aqueous cell culture medium prepared according to this method may be optionally dried to produce a powdered cell culture medium comprising the ethanolamine derivative or sequestered ethanolamine. In another embodiment, this disclosure provides a method of preparing an aqueous cell culture medium by combining a solvent, such as water, with a powdered cell culture medium comprising one or more amino acids and an ethanolamine derivative or ethanolamine that has been complexed with a sequestering agent ("sequestered ethanolamine").

Similarly, this disclosure provides a powdered cell culture medium prepared according to the methods described herein. In one embodiment, the powdered cell culture medium comprises an ethanolamine derivative or ethanolamine that has been complexed with a sequestering agent ("sequestered ethanolamine") and one or more amino acids. The powdered cell culture medium optionally comprises other ingredients, such as a carbohydrate (e.g., glucose).

In certain embodiments, the cell culture medium is a single component media containing one or more labile compounds such as: ethanolamine, growth factors, cytokines, etc. In one embodiment, the cell culture medium is protein free. In another embodiment, the cell culture medium is protein free and does not contain lipids, hydrolysates, or growth factors. In some embodiments, the cell culture medium may be suitable for culturing a bacterial cell, a yeast cell, a plant cell, algal cell, or an animal cell, such as an insect cell (e.g., *Drosophila* cells, *Spodoptera* cells or *Trichoplusia* cells), a nematode cell (e.g., *C. elegans* cells) or a mammalian cell (e.g., CHO cells, COS cells, VERO cells, BHK cells, AE-1 cells, SP2/0 cells, L5.1 cells, PerC6, hybridoma cells, or other human cells).

In another aspect, the disclosure provides a method of culturing a cell, comprising contacting the cell with a cell culture medium comprising one or more labile compounds such as an ethanolamine derivative, a sequestered ethanolamine, a sequestered growth factor, a sequestered cytokine, etc. under conditions supporting the cultivation of the cell. In some embodiments the cell may be a parent cell, while in other embodiments, the cell may be a recombinant cell carrying a gene of interest, or a diseased cell such as a cancer cell, etc. Any cell may be cultured according to the present methods, for example, bacterial cells, yeast cells, or eukaryotic cells such as algal cells, plant cells or particularly, animal cells. In one embodiment, the animal cell is a mammalian cell. In some embodiments, the medium is used for cultivating a mammalian cell, including human cells and/or tissues, including but not limited to CHO (Chinese Hamster Ovary) cells, COS cells, VERO cells, BHK cells, AE-1 cells, SP2/0 cells, L5.1 cells, PerC6, hybridoma cells, or any other mammalian cell, an insect cell including but not limited to, *Drosophila* cells, *Spodoptera* cells or *Trichoplusia* cells, a nematode cell including but not limited to *C. elegans* cells, etc.

Another aspect provides a composition comprising a cell culture medium comprising one or more labile compounds such as an ethanolamine derivative, a sequestered ethanolamine, a sequestered growth factor, a sequestered cytokine, etc., and at least one cell, as described above. In one embodiment, the cell is a mammalian cell. In one preferred embodiment, the mammalian cell is a CHO cell. In yet another preferred embodiment, the CHO cell is a recombinant CHO cell carrying a gene of interest.

Yet another aspect is directed to kits for use in the cultivation of a cell. The kit may comprise one or more containers containing a cell culture medium comprising one or more labile compounds such as an ethanolamine derivative, a sequestered ethanolamine, a sequestered growth factor, a sequestered cytokine, etc., optionally one or more amino acids, and one or more cells or cell types. The kit, in addition, may optionally comprise at least one additional component selected from at least one growth factor, at least one culture medium supplement, at least one animal tissue extract, at least one animal organ extract, at least one animal gland extract, at least one enzyme, at least one protein, at least one vitamin, at least one cytokine, at least one lipid, at least one trace element, at least one extracellular matrix component, at least one buffer, at least one antibiotic, and at least one viral inhibitor.

Another aspect is directed to methods of producing a virus using the media described herein. Specifically, the method may comprise (a) contacting a cell (e.g., a mammalian cell) with a virus under conditions suitable to promote the infection of the cell by the virus; and (b) cultivating the cell in the cell culture medium comprising one or more labile compounds such as an ethanolamine derivative, a sequestered ethanolamine, a sequestered growth factor, a sequestered cytokine, etc., under conditions suitable to promote the production of virus, a viral particle (VLP) or a vaccine. In one embodiment, the cell may be a mammalian cell, such as a CHO cell.

In yet another aspect, the disclosure provides methods of producing a polypeptide using the media described herein. Specifically, the method comprises cultivating a cell that has been genetically engineered to produce a polypeptide in a cell culture medium comprising one or more labile compounds such as an ethanolamine derivative, a sequestered ethanolamine, a sequestered growth factor, a sequestered cytokine, etc., under conditions suitable for expression of the polypeptide by the cell. In one embodiment, the cell is a mammalian cell, such as a CHO cell.

Microencapsulation may extend storage conditions of sensitive compounds like ethanolamine, vitamins, growth factors, etc., which may positively impact shipping and handling of dry media formulations like AGT™, etc., at room temperature rather than at lower temperatures (for e.g., refrigeration or dry ice), which can decrease shipping costs. Microencapsulation of labile compounds in dry format media may therefore be viewed as a contribution to green technology, for the cheaper handling and storage of dry format cell culture media.

DESCRIPTION OF THE DRAWINGS

FIG. 3A shows the making of alginate microbeads using $CaCl_2$ for microencapsulation, which were formed successfully using two procedures: i) using the needle and syringe method, and ii) the spray mist method, at the bench scale. For scale-up, the following equipment may be used: an encapsulation machine, a jet cutter, a vibrational nozzle, a electrostatic generator or a coacervation mixer. FIG. 3B shows the characteristics of the alginate beads generated under different microencapsulation setting parameters. Optimal $CaCl_2$ and alginate concentrations were identified. Homogeneity testing suggested non-segregation of microcapsules in the AGT™ dry format. Microbead loaded at 1000× yielded acceptable bead characteristics. FIG. 3C shows studies using vitamin B12 as the labile substance. The standard and the reduced beads showed the best results and were used for further experiments.

DETAILED DESCRIPTION

Figure 1A:
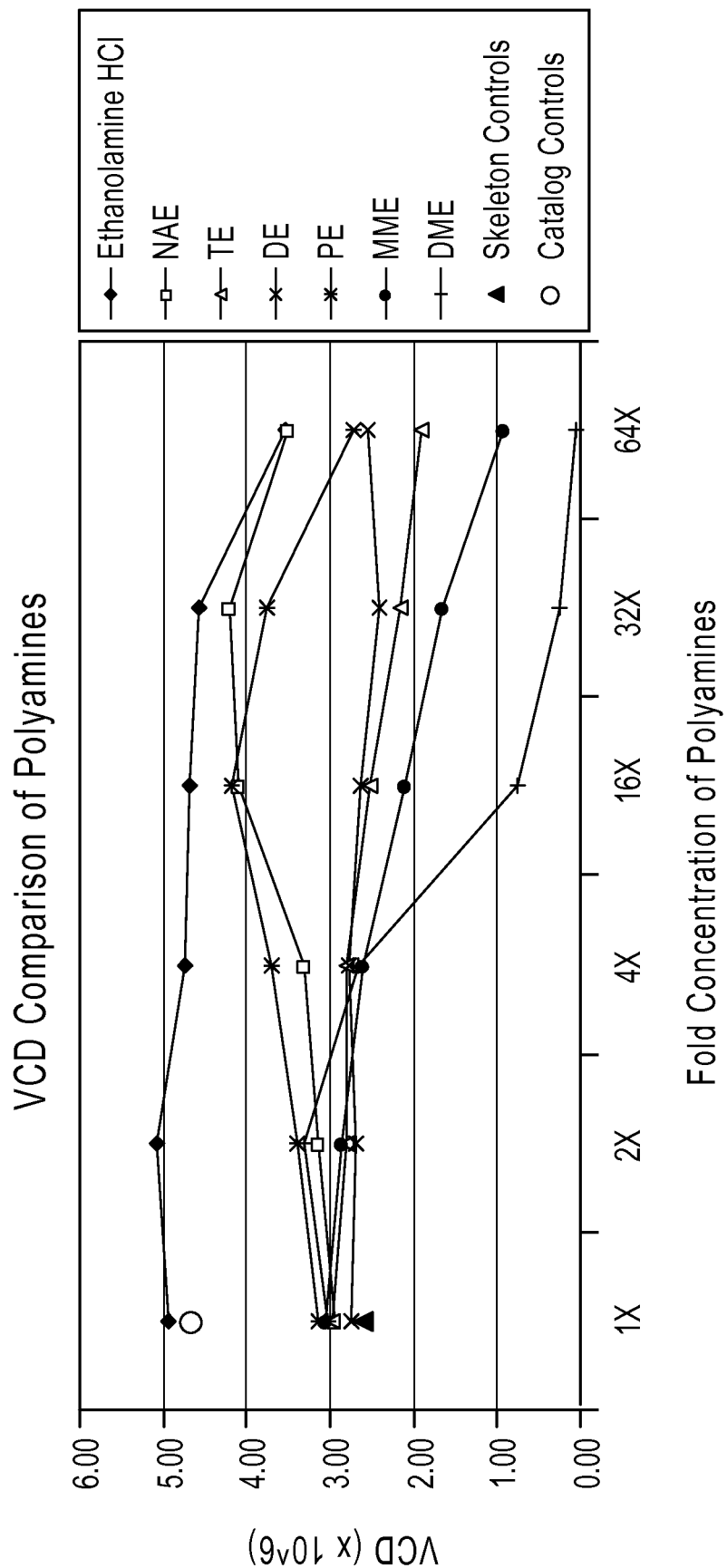
FIGS. 1A and 1B show the viable cell density (VCD) of cells (DG44-EPO) grown in media containing a range of ethanolamine derivatives (x-axis), tested for cell culture potency, including phosphorylethanolamine (PE), triethanolamine (TE), diethanolamine (DE), monomethylethanolamine (MME), dimethylethanolamine (DME), and N-acetylethanolaine (NAE). NAE and PE were preferred derivatized ethanolamines that are stable in media. See Example 2 for details.

Reference will now be made in detail to various exemplary embodiments. It is to be understood that the following detailed description is provided to give the reader a fuller understanding of certain embodiments, features, and details of aspects of the disclosure, and should not be interpreted as a limitation of the scope of the disclosure.

1. Definitions

In order that the present disclosure may be more readily understood, certain terms are first defined. Additional definitions are set forth throughout the detailed description.

The term "advanced granulation technology" or AGT, as used in this application refers to a process of preparing cell culture medium that involves spraying of aqueous solutions of concentrated medium components onto air suspended attrited powdered medium components and rapid evaporation of water, resulting in homogenous distribution of ingredients throughout the resulting aggregated granules, called granulated powder, which has typical characteristics of large granule size and less dusting. See Fike et al., Cytotechnology, 2006, 36:33-39, which is hereby incorporated by reference in its entirety. The term "advanced powder media" or APM refers to a dry powder media format with advantageous properties in that the particle size is not as fine as DPM powder. It has several of AGT's advantageous properties.

The term "susceptible compound" or "sensitive compound" or "labile compound" as used in this application refers to substance, chemical or compound to be protected using the methods in this disclosure; that is either by encapsulation (sequestering) or by forming an N-acetyl bond with an amine-moiety containing chemical. Examples of such compounds in cell culture media are: vitamins, cytokines, growth factors, peptides, and hormones.

The term "ethanolamine derivative" as used in this application refers to an ethanolamine compound in which the amine group of ethanolamine is stabilized by a covalent linkage, such as an amide bond.

The term "sequestering agent" as used in this application refers to the protection, separation, encapsulation or sequestering of susceptible chemicals or compounds from conditions that enhance degradation, or from other chemicals such as amino acids; trace elements such as manganese, copper, etc.; inorganic buffers such as sodium bicarbonate and other sodium phosphates; and organic buffers such as MOPS, HEPES, PIPES, etc. which react slowly with the susceptible compound, thereby losing their desirable properties over time. The terms "protect" or "separate" or "sequester" or "encapsulate" may have been used interchangeably in the disclosure, and convey the concept of protecting the susceptible chemical or compound from degrading conditions or chemicals. The "soluble sequestering agent" itself may be soluble upon reconstitution with an aqueous medium, whereupon it releases the "sensitive" encapsulated material. Or, the "insoluble sequestering agent" may be insoluble upon reconstitution with an aqueous medium, whereupon after releasing the "sensitive" encapsulated material, it can be removed by means such as filtration, decanting, etc. from the reconstituted endproduct. Examples of insoluble sequestering agents include, but are not limited to, alginate, poly-L-lactic acid (PLL), chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, carrageenan and so on. Other scaffolding matrices that may be used for microencapsulation include poly-glycolic acid, PLGA (poly-lactic-co-glycolic acid), collagen, polyhydroxyalkanoates (PHA), poly-ε-caprolactone, poly-ortho esters, poly-anhydrides, poly-phosphazenes, poly-amino acids, polydimethylsiloxane, polyurethanes, poly-tetrafluoroethylene, poly-ethylene, polysulphone, poly-methyl methacrylate, poly-2-hydroxyethylmethacrylate, polyamides, polypropylene, poly-vinyl chloride, polystyrene, poly-vinyl pyrrolidone, etc.

Examples of soluble sequestering agents include, but are not limited to, hexose sugars like glucose, mannose, galactose, fructose, disaccharides like sucrose, other soluble oligosaccharides and soluble polysaccharides.

In one embodiment, the composition is a cell culture medium comprising one or more amino acids and ethanolamine. The cell culture medium is preferably a powdered cell culture medium. In one embodiment, the powdered cell culture medium is an advanced granulation technology (AGT) cell culture medium. The media also refers to concentrated feed supplements, concentrated media, and in some instances, liquid media, as applicable.

The terms "cell culture" or "culture" as used in this application refer to the maintenance of cells in an artificial (e.g., an in vitro) environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

The term "cultivation" as used in this application refers to the maintenance of cells in an artificial environment under conditions favoring growth, differentiation, or continued viability, in an active or quiescent state, of the cells. Thus, "cultivation" may be used interchangeably with "cell culture" or any of its synonyms described above.

The terms, "cell culture medium," "culture medium," or "medium" (and in each case plural media) as used in this application refer to a nutritive composition that supports the cultivation and/or growth of cells. The cell culture medium may be a complete formulation, i.e., a cell culture medium that requires no supplementation to culture cells, may be an incomplete formulation, i.e., a cell culture medium that requires supplementation or may be a medium that may supplement an incomplete formulation or in the case of a complete formulation, may improve culture or culture results. The terms "cell culture medium," "culture medium," or "medium" (and in each case plural media) refer to unconditioned cell culture media that has not been incubated with cells, unless indicated otherwise from the context. As such, the terms "cell culture medium," "culture medium," or "medium" (and in each case plural media) are distinguished from "spent" or "conditioned" medium, which may contain many of the original components of the medium, as well as a variety of cellular metabolites and secreted proteins.

The term "extract" as used in this application refers to a composition comprising a component of a substance or a concentrated preparation of the subgroups of a substance, typically formed by treatment of the substance either mechanically (e.g., by pressure treatment) or chemically (e.g., by distillation, precipitation, enzymatic action or high salt treatment).

The term "increased ethanolamine stability" as used in this application refers to less degradation of ethanolamine as compared to a control composition containing ethanolamine in a non-derivative or non-sequestered form. For example, as used in the context of a powdered cell culture medium, the term "increased ethanolamine stability" refers to less degradation of ethanolamine as compared to a control that has the same ingredients except that in the control medium the ethanolamine is present in a non-derivative or non-sequestered form (referred to as "control medium"). The control medium may also contain one or more additional ingredients, such as, proline that is used as a dispersant. For purposes of measuring whether a cell culture medium has increased stability, as used in this application, the degradation of ethanolamine is measured after storing the powdered cell culture medium at different temperatures (e.g., 4° C. and room temperature) for 7 days, reconstituting the powdered cell culture medium with water for injection (WFI), and measuring the concentration (mg/L) of ethanolamine in the reconstituted cell culture medium. A smaller % difference in the concentration of ethanolamine in the culture medium stored at the different temperatures indicates less degradation of ethanolamine and, therefore, increased stability. For example, if a powdered cell culture medium comprising one or more amino acids and the ethanolamine derivative or stabilized ethanolamine exhibits a drop in ethanolamine concentration from 100 mg/L at 4° C. to 95 mg/L at room temperature (5% difference) and the control medium exhibits a drop in ethanolamine from 50 mg/L at 4° C. to 25 mg/L at room temperature (50% difference), then the powdered cell culture medium comprising one or more amino acids and the stabilized ethanolamine has increased ethanolamine stability because it exhibits less degradation of ethanolamine (smaller % difference) than the control medium. You would measure NAE at both temperatures to see if any difference. NAE is detected using different analytical criteria than ethanolamine. See FIGS. 2A and 2B and Example The term "ingredient" as used in this application refers to any compound, whether of chemical or biological origin, that can be used in cell culture media to maintain or promote the growth of proliferation of cells. The terms "component," "nutrient" and "ingredient" can be used interchangeably and are all meant to refer to such compounds. Typical ingredients that can be used in cell culture media include amino acids, salts, metals, sugars, carbohydrates, lipids, nucleic acids, hormones, vitamins, fatty acids, proteins and the like. Other ingredients that promote or maintain cultivation of cells ex vivo can be selected by those of skill in the art, in accordance with the particular need.

The term "powder" or "powdered" as used in this application refers to a composition that is present in granular form, which may or may not be complexed or agglomerated with a solvent such as water or serum. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

The term "sequestering agent" as used in this application refers to an agent that protects ethanolamine or otherwise confers increased ethanolamine stability. Additionally, encapsulation also provides for controlled release.

The term "stabilized ethanolamine" as used in this application refers to ethanolamine that has been complexed with a sequestering agent.

A "1× formulation" refers to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L of L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See Cell Culture Technology for Pharmaceutical and Cell-Based Therapies, 42-50 (Sadettin Ozturk and Wei-Shou Hu eds., Taylor and Francis Group 2006), which is incorporated by reference herein in its entirety. The osmolarity and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare 1× formulation, above). A "10× formulation" may contain a number of additional ingredients at a concentration about 10 times that found in the 1× culture medium. As will be readily apparent, "5× formulation," "25× formulation," "50× formulation," "100× formulation," "500× formulation," and "1000× formulation" designate solutions that contain ingredients at about 5-25-, 50-, 100-, 500-, or 1000-fold concentrations, respectively, as compared to a 1× cell culture medium. Again, the osmolarity and pH of the media formulation and concentrated solution may vary. A formulation may contain components or ingredients at 1× with respect to a particular cell culture protocol, but at a concentration, for example, 2, 2.5, 5, 6.7, 9, 12 etc. × with respect to a different culture protocol or different base medium.

The present disclosure concerns the stabilization of ethanolamine in dry and liquid form. One aspect concerns methods of increasing the stability of ethanolamine in cell culture medium, and particularly dry format (or powdered) cell culture medium. Ethanolamine is less stable in a dry format than in liquid format. In dry format, combining ethanolamine with a carbohydrate (e.g., glucose) alone (without amino acids) results in little or no ethanolamine degradation. However, in the presence of amino acids, significant ethanolamine degradation occurs rapidly especially at elevated temperatures (e.g. 30° C.).

Applicants have discovered methods of reducing ethanolamine degradation. Although these methods are primarily exemplified within the context of cell culture media, it is understood that they can be applied in any context where increased ethanolamine stability is desired in any dry or semi-dry format. As ethanolamine is used in other fields, such as detergents, pharmaceuticals, and cosmetics, as well as in methods of treating water (to control corrosion) and removing acids from a gas, the skilled artisan can similarly adapt the methods described in this application to stabilize ethanolamine in these other applications.

One aspect is directed to methods of increasing ethanolamine stability by using ethanolamine derivatives having a covalent linkage at the ethanolamine amine group.

Another method of increasing ethanolamine stability involves forming a complex between ethanolamine and a sequestering agent. In one embodiment, the sequestering agent is a ketone- or aldehyde-containing molecule, such as a sugar (e.g., glucose), or a derivative thereof, or a keto acid. In another embodiment, ethanolamine is embedded or encapsulated within the sequestering agent.

1. Covalent Linkage of Amine Group

As noted above, one way of to increase the stability of ethanolamine is to use an ethanolamine derivative in which the amine group of ethanolamine is stabilized by a covalent linkage, such as an amide (or peptide) bond. An amide bond is a covalent bond formed between two molecules when the carboxyl group of one molecule reacts with the amine group of the other molecule, thereby releasing a molecule of water. In one embodiment, the ethanolamine derivative has the following formula:

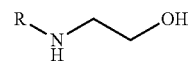

wherein R is an acetyl group or an amino acid.

When R is an acetyl group, the ethanolamine derivative is N-acetylethanolamine (NAE) and has the following the structure:

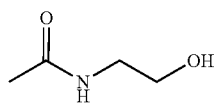

Similar to ethanolamine exemplified herein, other substances that contain amines and may sometimes be sensitive in certain conditions may include alkanolamines or polyamines like spermine, spermidine, putrescine, cadaverine, anandamide, polylysine, trilysine, diallyl dimethyl ammonium chloride polyallylamine, polyvinylamine, polyethylamine, polybutylamine, polyisobutylamine, polypropylamine hexamethylene diamine, ethylenediamine, N-ethylethylenediamine, N,N'-diethylethylenediamine, N-ethylethanolamine, triethylenediamine, N-methylmorpholine, pentamethyl diethylenetriamine, dimethylcyclohexylamine, tetramethylethylenediamine, 1-methyl-4-dimethylaminoethyl-piperazine, 3-methoxy-N-dimethyl-propylamine, N-ethylmorpholine, diethylethanolamine, N-cocomorpholine, N,N-dimethyl-N',N'-dimethylisopropylpropylene diamine, N,N-diethyl-3-diethyl aminopropylamine, dimethyl-benzyl amine, etc. and the acetylation method described herein for stabilization could be applied to these compounds as well.

In addition, R can also be any amino acid, including, but not limited to alanine, arginine, asparagine, aspartic acid, cysteine, glutamic acid, glutamine, glycine, histidine, isoleucine, leucine, lysine, methionine, phenylalanine, proline, hydroxyproline, serine, threonine, tryptophan, tyrosine, and valine. In one embodiment the amino acid has a non-polar side chain. In another embodiment, the amino acid is glycine, alanine, valine, leucine, or isoleucine.

In another embodiment, the ethanolamine derivative is 1,3,5-tris(2-hydroxyethyl)-s-triazine (Grotan). Grotan can be formed by reacting ethanolamine with formaldehyde.

Thus, one aspect of this disclosure relates to a method of increasing the stability of ethanolamine, in a composition, the method comprising:

combining an ethanolamine, as described herein, with say an acetyl compound, wherein N-acetylethanolamine exhibits increased stability. Another aspect relates to a composition comprising an ethanolamine derivative as described herein, wherein the composition exhibits increased ethanolamine stability. In one embodiment, the composition is a cell culture medium comprising one or more amino acids.

2. Interaction with a Ketone- or Aldehyde-Containing Molecule

It is also possible to stabilize ethanolamine through an interaction with a encapsulating or sequestering agent, where the sequestering agent is a sugar, a ketone- or aldehyde-containing molecule, particularly one that is involved in a metabolic pathway, such as a sugar or a keto acid. This type of sequestering may result in a type of protection or encapsulation wherein the microcapsule dissolves, or substantially dissolves upon reconstitution with solute, and the concentration of the sugar, keto or aldehyde in the capsule is taken into account for final media utilization. Without intending to be bound by any theory, it appears that the ketone- or aldehyde-containing or sugar molecule forms a crystal structure around the ethanolamine when combined with ethanolamine and the crystal structure helps to protect ethanolamine from degradation, particularly when the ethanolamine is in a dry format.

In one embodiment the sequestering agent is a sugar. In one embodiment, the sugar is a hexose sugar, such as allose, altrose, fructose, galactose, glucose, gulose, idose, mannose, sorbose, talose, or tagatose, or a derivative thereof, such as a sugar alcohol, an amino sugar, an uronic acid, or a phosphorylated sugar. In another embodiment, the sugar is a pentose sugar, such as arabinose, ribose, ribulose, xylose, xylulose, or lyxose, or a derivative thereof, such as a sugar alcohol, an amino sugar, an uronic acid, or a phosphorylated sugar. In another embodiment, the sugar is a tetrose sugar, such as erythrulose, erythrose, or threose or a derivative thereof, such as a sugar alcohol, an amino sugar, an uronic acid, or a phosphorylated sugar. In yet another embodiment, the sugar is a triose, such as glyceraldehyde or dihydroxyacetone, or a derivative thereof, such as a sugar alcohol, an amino sugar, an uronic acid, or a phosphorylated sugar.

Sugar alcohols that can be used to stabilize ethanolamine include, but are not limited to, allitol, altritol, fructitol, galactitol, glucitol, gulitol, iditol, mannitol, sorbitol, talitol, tagatitol, arabinitol, ribitol, ribulitol, xylitol, xylulitol, lyxitol, erythrulitol, erythritol, or threitol. Amino sugars that can be used to stabilize ethanolamine include, but are not limited to allosamine, altrosamine, fructosamine, galactosamine, glucosamine, gulosamine, idosamine, mannosamine, sorbosamine, talosamine, tagatosamine, arabinosamine, ribosamine, ribulosamine, xylosamine, xylulosamine, lyxosamine, erythrulosamine, erythrosamine, or threosamine. Uronic acids that can be used to stabilize ethanolamine include, but are not limited to, alluronic acid, altruronic acid, fructuronic acid, galacturonic acid, glucuronic acid, guluronic acid, iduronic acid, mannuronic acid, sorburonic acid, taluronic acid, tagaturonic acid, arabinuronic acid, riburonic acid, ribuluronic acid, xyluronic acid, xyluluronic acid, lyxuronic acid, erythruluronic acid, erythruronic acid, or threuronic acid. Phosphorylated sugars that can be used to stabilize ethanolamine include, but are not limited to glyceraldehyde 3-phosphate and dihydroxyacetone phosphate.

In other embodiments, the sugar is a disaccharide, such as maltose, lactose, lactulose, trehalose, cellobiose, or sucrose. In another embodiment, the sequestering agent is a keto acid, or a sugar, including but not limited to 1) a sugar such as a hexose like glucose, mannose, etc, 2) a beta keto acid, such as acetoacetic acid, or 3) a gamma-keto acid, such as levulinic acid, or 4) an alpha-keto acid, such as pyruvic acid, oxaloacetic acid, glycolic acid, or ketoglutaric acid, or 5) sugar-like derivatives like maltodextrins, other oligo- or polysaccharides, gums, arabinogalactan, etc.

A complex between ethanolamine and a ketone- or aldehyde-containing molecule can be formed by dissolving ethanolamine in water and then adding to a given weight of the ketone- or aldehyde-containing molecule. The ethanolamine/ketone or aldehyde/sugar/sugar derivative/water mixture is kneaded with an instrument, such as a spatula, until it forms a paste-like consistency. The paste is spread flat and dried overnight under a hood, optionally followed by a final drying in a dessicator. The dried mixture is optionally fitzmilled at desired sizing specifications before blending it with other compositions, such as a powdered cell culture medium. When sugars like glucose are part of the encapsulation matrix, the glucose concentration is adjusted such that only a part of the glucose is used for preparing the matrix and the final concentration of the glucose upon reconstitution of the media is maintained at an ideal.

In one aspect, this disclosure relates to a method of increasing the stability of ethanolamine in a composition, the method comprising:

combining ethanolamine complexed with a sequestering agent ("sequestered ethanolamine") with the composition, wherein the composition comprising the sequestered ethanolamine exhibits increased ethanolamine stability and wherein the sequestering agent comprises a ketone- or aldehyde-containing molecule, as described herein. The method optionally further comprises before the combining step a step of complexing ethanolamine with the ketone- or aldehyde-containing molecule to produce the sequestered ethanolamine. In one embodiment, the ketone- or aldehyde containing molecule is a sugar, or a derivative thereof, or a keto acid. In one embodiment, the composition is a cell culture medium comprising one or more amino acids. The cell culture medium is preferably a powdered cell culture medium. In one embodiment, the powdered cell culture medium is an advanced granulation technology cell culture medium. The ability of a ketone- or aldehyde-containing molecule to increase ethanolamine stability can be evaluated using techniques known in the art, including the methods disclosed in this application.

Another aspect relates to a composition comprising a ketone- or aldehyde-containing molecule, as described herein, wherein the composition exhibits increased ethanolamine stability. In one embodiment, the ketone- or aldehyde containing molecule is a sugar, or a derivative thereof, or a keto acid. In one embodiment, the composition is a cell culture medium comprising one or more amino acids. In one embodiment, the cell culture medium further comprises a carbohydrate. In another embodiment, the cell culture medium is protein free. The cell culture medium is preferably a powdered cell culture medium. In one embodiment, the powdered cell culture medium is an advanced granulation technology cell culture medium.

3. Encapsulation

Another way to stabilize ethanolamine or other unstable media compounds is to encapsulate or embed them within a sequestering agent. Without intending to be bound by any theory, it appears that encapsulating or embedding sensitive components such as ethanolamine within another molecule reduces ethanolamine's direct contact with other components or conditions that promote ethanolamine's degradation, or reduces its stability. Automated or controllable systems are available for the encapsulation process as well, for example, co-extrusion using an encapsulation machine, electrostatic bead generator, the vibrating nozzle technique, jet cutter technology, etc. Parameters that may impact the functional properties of the bead may include the microcapsule concentration, the % CaCl2, the % alginate, release rate, solubility, the drying protocol, the micobead size, homogeneity, ethanolamine protection, coating procedure (PLL, etc), and so on.

Applicants have discovered methods of reducing ethanolamine degradation by the microencapsulation method. Although these methods are primarily exemplified within the context of ethanolamine stabilization, it can be used to stabilize any susceptible chemical or compound that needs to be stabilized. In particular, context for stability in cell culture media have been referred to in this instance and in the examples. However, it is understood that the microencapsulation method can be used for stabilizing any susceptible compound including but not limited to vitamins, unstable amino acids, cytokines, growth factors, sensitive and valuable proteins or peptides, etc. and for enhanced delivery of the stabilized compound, and can be applied to fields beyond cell culture media development. For instance, the encapsulation of dendrimers may be applicable in industrial applications, pharmaceuticals (drug delivery), nutraceuticals, food supplements, vitamin enriched formulations, cosmetic industry, enzyme industry, buffers as in the food industry, detergents, etc. As these methods and compositions can be used in other fields, the skilled artisan can similarly adapt the methods described in this application to stabilize other susceptible or degradation-prone compounds in other applications.

Figure 6:
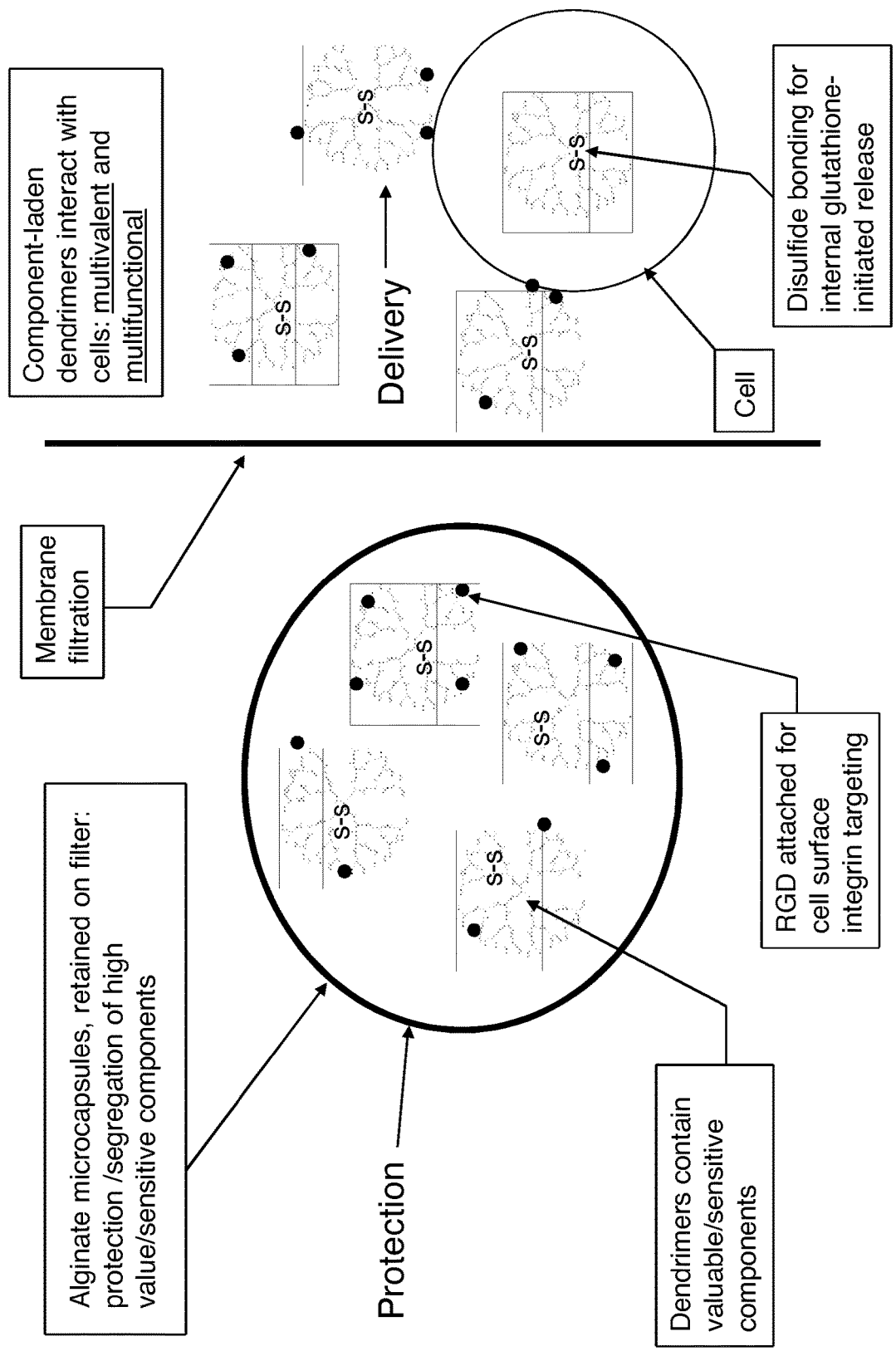
FIG. 6: Microencapsulated dendrimer component delivery system. This figure shows how microencapsulated dendrimers work. Alginate protects the dendrimers and upon reconstitution, releases the dendrimers with the sensitive substance. Alginate is retained on the membrane filter during filtration. In one embodiment, the exposed dendrimer can target a labile substance such as ethanolamine, or any other molecule, to a cell due to the presence of cell recognition sites present on the dendrimer, thereby improving availability of sensitive or low-concentration substances such as growth factors, vitamins, etc. to the growing cell.

In one embodiment, the sequestering agent like alginate is used to encapsulate or embed an ethanolamine-dendrimer complex. Dendrimers are hyper-branched synthetic macromolecules that can be made using controlled sequential processes to give them defined structural and molecular weight characteristics. Reviewed in Astruc et al., Chem. Rev. 2010, 110:1857-1959, which is hereby incorporated by reference in its entirety. Dendrimers have a central core, repeated branches, and surface functional groups. The repeated branches are organized in a series of concentric layers called generations. The number of surface functional groups, molecular weight and size of dendrimers increase exponentially as a function of generation (the number of layers) of the polymer and can be controlled during synthesis. Different types of dendrimers can be synthesized based on the core structure that initiates the polymerization process. The microencapsulated dendrimers of this disclosure are described in FIG. 6. In one embodiment, the dendrimer is encapsulated in a capsule, for e.g., in alginate. Alginate protects the dendrimers and upon reconstitution, releases the dendrimers with the sensitive substance. Alginate is retained on the membrane filter during filtration. The exposed dendrimer can target the sensitive substance to a cell due to the presence of cell recognition sites present on the dendrimer, thereby improving availability of sensitive or low-concentration substances such as growth factors, vitamins, etc. to the cell. As one of skill in the art would know, any encapsulating agent besides alginate may be used to protect the dendrimer, for instance, alginate, poly-L-lactic acid (PLL), chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, carrageenan and so on. Other scaffolding matrices that may be used for microencapsulation include poly-glycolic acid, PLGA (poly-lactic-co-glycolic acid), collagen, polyhydroxyalkanoates (PHA), poly-ε-caprolactone, poly-ortho esters, poly-anhydrides, polyphosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, etc.

The dendrimer core structures dictate several characteristics of the molecule such as the overall shape, density and surface functionality (Tomalia et al., Chem. Int. Ed. Engl., 1990, 29:5305. Spherical dendrimers generally have ammonia as a trivalent initiator core or ethylenediamine (EDA) as a tetravalent initiator core. Recently described rod-shaped dendrimers (Yin et al., J. Am. Chem. Soc., 1998, 120:2678) use polyethyleneimine linear cores of varying lengths; the longer the core, the longer the rod. Dendritic macromolecules are available commercially in kilogram quantities and can be produced under current good manufacturing processes (GMP) for certain biotechnology applications.

Dendrimers are generally synthesized by convergent or divergent routes. In the divergent route, the assembly begins with the central core and extends outward by series of reactions. Each additional series of reactions leads to a higher generation dendrimer. In the convergent route, assembly begins at the periphery and builds inward with the branches eventually being attached to the core. Dendrimer can also be synthesized via click chemistry (see e.g., U.S.

Patent Application Publication No. 20050222427 and PCT/US03/17311, both of which are hereby incorporated by reference in their entirety), using Diels-Alder reactions, thiol-ene reactions, and azide-alkyne reactions. See Franc et al., Chem. Eur. J., 2009, 15(23):5631-39; Killops et al., J Am. Chem. Soc., 2008, 130(15):5062-64; Franc et al., Chem. Comm., 2008, 5267-76; and Carlmark et al., Chem. Soc. Rev., 2009, 38:352-62, all of which are hereby incorporated by reference in their entirety.

Dendrimers have been used in many fields, including supramolecular chemistry, electrochemistry, photochemistry, nanoparticle synthesis pollution management, dye coloration, preparation of monomolecular membranes, curing of expoy resins, catalysis, drug delivery, and gene transfection. Cheng, et al., J. Pharm. Sciences, 2008, 97:123-43. Dendrimers typically have empty internal cavities or open conformations (for low generation dendrimers) that can be used to encapsulate compounds, such as therapeutic molecules. The presence of surface functional groups also helps to enhance the solubility of encapsulated compounds.

Numerous U.S. patents describe methods and compositions for producing dendrimers. Some exemplary patents are provided below as examples of dendrimer compositions that may be useful in the methods and compositions described in this application. These patents are merely illustrative examples and numerous other similar dendrimer compositions could be used in the methods and compositions described in this application.

U.S. Pat. Nos. 4,507,466, 4,558,120, 4,568,737, and 4,587,329, all of which are hereby incorporated by reference in their entirety, describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337, which is hereby incorporated by reference in its entirety, describes hydrolytically stable polymers. U.S. Pat. No. 4,694,064, which is hereby incorporated by reference in its entirety, describes rod-shaped dendrimers. U.S. Pat. No. 4,713,975, which is hereby incorporated by reference in its entirety, describes dense star polymers and their use to characterize surfaces of viruses, bacteria and proteins including enzymes. Bridged dense star polymers are described in U.S. Pat. No. 4,737,550, which is hereby incorporated by reference in its entirety. U.S. Pat. Nos. 4,857,599 and 4,871,779, which are hereby incorporated by reference in its entirety, describe dense star polymers on immobilized cores useful as ion-exchange resins, chelation resins and methods of making such polymers.

U.S. Pat. No. 5,338,532, which is hereby incorporated by reference in its entirety, is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

Other useful dendrimer type compositions are described in U.S. Pat. Nos. 5,387,617, 5,393,797, and 5,393,795, which are hereby incorporated by reference in their entirety, in which dense star polymers are modified by capping with a hydrophobic group capable of providing a hydrophobic outer shell. U.S. Pat. No. 5,527,524, which is hereby incorporated by reference in its entirety, discloses the use of amino terminated dendrimers in antibody conjugates.

The use of dendrimers as metal ion carriers is described in U.S. Pat. No. 5,560,929, which is hereby incorporated by reference in its entirety. U.S. Pat. No. 5,773,527, which is hereby incorporated by reference in its entirety, discloses non-crosslinked polybranched polymers having a comb-burst configuration and methods of making the same. U.S. Pat. No. 5,631,329, which is hereby incorporated by reference in its entirety, describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863, which is hereby incorporated by reference in its entirety, describes dendrimer networks containing lipophilic organosilicone and hydrophilic polyanicloamine nanoscopic domains. The networks are prepared from copolydendrimer precursors having PAMAM (hydrophilic) or polypropyleneimine interiors and organosilicon outer layers.

U.S. Pat. No. 5,795,582, which is hereby incorporated by reference in its entirety, describes the use of dendrimers as adjutants for influenza antigen. U.S. Pat. Nos. 5,898,005 and 5,861,319, which are hereby incorporated by reference in their entirety, describe specific immunobinding assays for determining concentration of an analyte. U.S. Pat. No. 5,661,025, which is hereby incorporated by reference in its entirety, provides details of a self-assembling polynucleotide delivery system comprising dendrimer polycation to aid in delivery of nucleotides to target site.

U.S. Pat. No. 6,471,968, which is hereby incorporated by reference in its entirety, describes the combination of two or more dendrimers, each with a specific functionality, a dendrimer single complex, such as a dendrimer complex comprising a polyamidoamine (PAMAM) dendrimer and a polypropylamine (POPAM) dendrimer.

In one embodiment, the dendrimer used in the methods described in this application is a polyamidoamine. Polyamidoamine, or PAMAM, is one of the most commonly used dendrimers in the biological field and is commercially available through multiple sources, including Dendritech Nanotechnologies Inc., which sells Starburst™ PAMAM dendrimers. Other dendrimers that can be used in the methods described in this application include, but are not limited to polypropyleneimine (PPI) dendrimers, phosphorous dendrimers, polylysine dendrimers, polypropylamine (POPAM) dendrimers, polyethylenimine dendrimers, iptycene dendrimers, aliphatic poly(ether) dendrimers, or aromatic polyether dendrimers. The ability of a dendrimer to increase ethanolamine stability can be evaluated using techniques known in the art, including the methods disclosed in this application.

In another embodiment, the sequestering agent used to encapsulate or embed ethanolamine is a microcapsule, for e.g., alginate. Microcapsules have been used for many purposes, including drug delivery and the immobilization of cells growing in cell culture to enhance cell growth and viability. See e.g., Serp et al., Biotechnology and Bioengineering, 2000, 70(1):41-53; Breguet et. al., Cytotechnology, 2007, 53:81-93; Chayosumrit et al., Biomaterials, 2010, 31:505-14; U.S. Pat. Nos. 7,482,152; and 7,740,861, all of which are incorporated by reference in their entirety.

In one embodiment, the microcapsule is comprised of material selected from alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan. Microcapsules are typically spherical particles having a diameter of 2 mm or less, usually within the diameter range of 0.05-1.5 mm. The ability of a microcapsule to increase ethanolamine stability can be evaluated using techniques known in the art, including the methods disclosed in this application.

After forming the microencapsulated ethanolamine, various solutions may be applied to provide additional layers to the microcapsules. For example, the microencapsulated ethanolamine can be coated with poly-L-lysine or polyornithine, optionally followed by an outer coating with a material selected from alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan.

In one embodiment, the microcapsule comprises alginate. Typically alginate microcapsules are formed by crosslinking between the polyanionic alginate and a divalent or trivalent polyvalent cation, such as calcium chloride. Other salts having divalent or trivalent cations, such as magnesium chloride, barium chloride, and aluminum sulfate can be used. In one embodiment, the alginate microcapsule further comprises a coating, such as poly-L-lysine or polyornithine.

In one aspect, this disclosure relates to a method of increasing the stability of ethanolamine in a composition, the method comprising:

combining ethanolamine complexed with a sequestering agent ("sequestered ethanolamine") with the composition, wherein the composition comprising the sequestered ethanolamine exhibits increased ethanolamine stability and wherein the sequestering agent comprises a dendrimer or a microcapsule, as described herein. The method optionally further comprises before the combining step a step of complexing ethanolamine with the dendrimer or the microcapsule to produce the sequestered ethanolamine.

In one embodiment, the microcapsule is comprised of material selected from alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan. The microcapsule is optionally coated, for example, with poly-L-lysine or polyornithine. In another embodiment, the dendrimer is a polyamidoamine dendrimer, a polypropyleneimine dendrimer, or a polypropylamine (POPAM) dendrimer. In one embodiment, the composition is a cell culture medium comprising one or more amino acids. The cell culture medium is preferably a powdered cell culture medium. In one embodiment, the powdered cell culture medium is an advanced granulation technology cell culture medium. The ability of a dendrimer or a microcapsule to stabilize ethanolamine can be evaluated using techniques known in the art, including the methods disclosed in this application.

This disclosure relates to a composition comprising a microcapsule containing a sensitive component or components or a microcapsule comprising a dendrimer-labile component or components complex to protect any labile substance, for e.g., ethanolamine. These microcapsules or microcapsule/dendrimer compositions may be dried and admixed with any dry format compositions to increase shelf life, increase storage, preserve the labile substance at ambient temperature, etc. In preferred embodiment, the microcapsule and/or dendrimer composition exhibits increased ethanolamine stability, and is dried and admixed with any dry format media compositions such as AGT, DPM, APM, etc. to increase the shelf life, increase storage handling, and to preserve the ethanolamine in the dry powder media at ambient temperature, etc. In one embodiment, the dry media composition comprises one or more amino acids as well in higher concentration, such as in media feeds, or in media supplements. In one embodiment, the cell culture medium further comprising dendrimeric compositions can specifically deliver to cells certain labile substances or a cell targeted substances efficiently. In a preferred embodiment, the labile substance or the targeted substance affects the cell it targets. In an embodiment, the effect may be cell growth, increased protein production, increased osmo-tolerance, or any other desired characteristic that requires the cell targeting or labile substance.

Detection of stabilized ethanolamine (labile substance): Can be done via LS-mass spectrometry (LS-MS) (FIG. 2B) for NAE, by separation of dry capsules or beads by sifting or any other means, and then dissolving the beads in a solvent. If the beads are insoluble, they can be filtered out, whereas if the beads are soluble there is nothing on the membrane filter, but in both cases, the labile substance, for e.g., ethanolamine can be detected via LS-MS in the supernatant.

Cell Culture Media

A cell culture medium is composed of a number of ingredients and these ingredients vary from one culture medium to another. A cell culture medium may be a complete formulation, i.e., a cell culture medium that requires no supplementation to culture cells, may be an incomplete formulation, i.e., a cell culture medium that requires supplementation or may be a supplement that is used to supplement an incomplete formulation or in the case of a complete formulation, may improve culture or culture results.

Generally, upon reconstitution, a cell culture medium will have solutes dissolved in solvent. The solutes provide an osmotic force to balance the osmotic pressure across the cell membrane (or wall). Additionally the solutes will provide nutrients for the cell. Some nutrients will be chemical fuel for cellular operations; some nutrients may be raw materials for the cell to use in anabolism; some nutrients may be machinery, such as enzymes or carriers that facilitate cellular metabolism; some nutrients may be binding agents that bind and buffer ingredients for cell use or that bind or sequester deleterious cell products.

Depending on the cell and the intended use of the cell, the ingredients of the cell culture medium will optimally be present at concentrations balanced to optimize cell culture performance. Performance will be measured in accordance with a one or more desired characteristics, for example, cell number, cell mass, cell density, 02 consumption, consumption of a culture ingredient, such as glucose or a nucleotide, production of a biomolecule, secretion of a biomolecule, formation of a waste product or by product, e.g., a metabolite, activity on an indicator or signal molecule, etc. Each or a selection of the ingredients will thus preferably optimized to a working concentration for the intended purpose.

A basal medium is typically used for maintenance of a cell culture, and can comprise a number of ingredients, including amino acids, vitamins, organic and inorganic salts, sugars and other components, each ingredient being present in an amount which supports the cultivation of the cell in vitro.

The media described herein that comprises stabilized ethanolamine can be a 1× formulation or can be concentrated, for example, as a 5×, 10×, 20×, 50×, 500×, or 1000× medium formulation. If the individual medium ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used. The media could be a basal media to which additional components need to be added, or a complete media which requires no additional additives and is capable of growing cells once reconstituted.

The media described herein that comprises stabilized ethanolamine can also be prepared in different formats, such as dry powder media (DPM) or as an advanced granulated preparation (AGT) that is complexed or agglomerated with a solvent such as water, vitamin solution, salt solution, lipid solution, or any solvent comprising one or more media components, or even serum and/or growth factors, over a fluid-bed apparatus, as described in U.S. Pat. No. 6,383,810, which is hereby incorporated by reference in its entirety, or otherwise prepared using advanced granulation technology—AGT™ (Invitrogen, Carlsbad, Calif.). See Fike et al., Cytotechnoloy, 2006, 36:33-39, which is hereby incorporated by reference in its entirety. It can also be prepared in an advanced powder media (APM, Life Technologies, CA) format. APM is a dry powder media format with some of the advantageous properties of AGT (agglomerated media: Advanced granulated technology) in that no additions such as sodium bicarbonate are required and pH adjustment is automatic and also not required. The media also refers to concentrated feed supplements, concentrated media, and in some instances, liquid media, as applicable.

In one embodiment, the reconstituted media from the dry powder that comprises stabilized ethanolamine results in an auto-pH and/or auto-osmolality medium comprising stabilized ethanolamine in that, it has balanced buffer concentrations and/or salt concentrations that contribute to automatically achieving a desired pH and osmolality suitable for growing a certain cell type without additional pH or salt concentration adjustment.

In another embodiment, or in a further embodiment, the reconstituted media from the dry powder that comprises stabilized ethanolamine results in a chemically defined cell culture medium. The presence of media proteins makes purification of recombinant protein difficult, time-consuming, and expensive and can also lead to reduced product yields and/or purity. Thus, in one embodiment, the cell culture medium would be serum-free and protein-free, yet complete, such that it can support the growth of a particular cell type. Alternately, the reconstituted media from the dry powder could be serum-free but still contain proteins derived from one or more non-animal derived sources (animal origin free—AOF) like from plants, yeast, algal, fungal, or recombinant sources such as bacteria, fungal, plant, yeast algal, etc. in the form of hydrolysates, or in the form of a purified protein or an hydrolysate fraction. In other instances, serum-free media may still contain one or more of a variety of animal-derived components, including albumin, fetuin, various hormones and other proteins. In another embodiment, the medium or media supplement is protein free and further, does not contain lipids, hydrolysates, or growth factors.

The media or supplements of this disclosure comprising protected labile molecules such as stabilized ethanolamine, or encapsulated ethanolamine, or encapsulated dendrimeric ethanolamine, can be used for fed-batch cultivation of cells, as they are not toxic for the growth of cells (see examples).

Fed-batch cultivation of cells is typically used for industrial production of biomolecules, such as proteins to increase cell concentration and to extend culture lifetime for a high product concentration and volumetric productivity. Fed-batch cultures involve the controlled addition of one or more nutrients, or feeds, such as glucose, to a basal medium. The nutrients or feeds used may comprise the protected, labile molecules described above, in this disclosure. The nutrient(s) may help to control the growth of the cell culture by preventing nutrient depletion or accumulation and byproduct accumulation, thereby maintaining important parameters, such as osmolality and $CO_2$ concentration, within levels that promote cell growth or minimize cell death for optimal product expression.

Cells and Viruses

Media containing an ethanolamine derivative or ethanolamine protected with a sequestering agent, as described herein, can also be used to culture a variety of cells. In one embodiment, the media is used to culture eukaryotic cells, including plant or animal cells, such as mammalian cells, fish cells, insect cells, algal cells, amphibian cells or avian cells or to produce viruses, virus-like particles.

Mammalian cells that can be cultured with the media described herein include primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PK1 cells, PK(15) cells, GH1 cells, GH3 cells, L2 cells, LLC-RC 256 cells, MH1C1 cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiC11 cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDM1C3 cells, KLN2O5 cells, McCoy cells, Mouse L cells, Strain 2071 (Mouse L) cells, L-M strain (Mouse L) cells, L-MTK-(Mouse L) cells, NCTC clones 2472 and 2555, SCC-PSA1 cells, Swiss/3T3 cells, Indian muntjac cells, SIRC cells, CII cells, and Jensen cells, or derivatives thereof).

Eukaryotic cells, including algal cells, may also be cultivated in the media compositions of this disclosure comprising stabilized ethanolamine to produce biofuels, under suitable conditions for growth and biofuel production.

Cells supported by the culture medium described herein can also be derived from any animal, preferably a mammal, and most preferably a mouse or a human. Cells cultured according to the methods disclosed herein may be normal cells, diseased cells, transformed cells, mutant cells, somatic cells, germ cells, stem cells, precursor cells or embryonic cells, any of which may be established or transformed cell lines or obtained from natural sources. Cells may be used for experimental purposes or for production of useful components.

In one embodiment, the media described herein is used to culture Chinese Hamster Ovary (CHO) cells, including recombinant CHO cells or CHO-derived cell lines like CHOS, CHOK1, DG44, RevO, etc. The term CHO cell includes reference to recombinant CHO cells and to all CHO-derived cell lines described. CHO cells have been classified as both epithelial and fibroblast cells derived from the Chinese hamster ovary. A cell line started from Chinese hamster ovary (CHO-K1) (Kao, F.-T. And Puck, T. T., Proc. Natl. Acad. Sci. USA 60: 1275-1281 (1968) has been in culture for many years but its identity is still not confirmed. Most biopharmaceuticals currently produce proteins in CHO cells for many advantages that the cell line has, such as human-like glycosylation patterns, precise post-translation modification and low risk for transmission of human viruses.

Cultivation of Cells

Cells supported by the culture medium described herein can be cultivated according to the experimental conditions determined by the investigator. It is to be understood that the optimal plating and culture conditions for a given animal cell type can be determined by one of ordinary skill in the art using only routine experimentation. For routine monolayer culture conditions, using the cell culture media described herein, cells can be plated onto the surface of culture vessels without attachment factors. Alternatively, the vessels can be precoated with natural, recombinant or synthetic attachment factors or peptide fragments (e. g., collagen, fibronectin, vitronectin, laminin and the like, or natural or synthetic fragments thereof), which are available commercially for example from Life Technologies, Corp. (Carlsbad, Calif. R&D Systems, Inc. (Rochester, Minn.), Genzyme (Cambridge, Mass.) and Sigma (St. Louis, Mo.). Cells can also be seeded into or onto a natural or synthetic three-dimensional support matrix such as a preformed collagen gel or a synthetic biopolymeric material. For suspension cultivation, cells are typically suspended in the culture media described herein and introduced into a culture vessel that facilitates cultivation of the cells in suspension, such as a spinner flask, perfusion apparatus, or bioreactor. Ideally, agitation of the media and the suspended cells will be minimized to avoid denaturation of media components and shearing of the cells during cultivation.

The cell seeding densities for each experimental condition can be optimized for the specific culture conditions being used. For routine monolayer culture in plastic culture vessels, an initial seeding density of $1-5\times10^5$ cells/cm2 is preferable, while for suspension cultivation a higher seeding density (e. g., $5-20\times10^5$ cells/cm2) may be used.

Mammalian cells are typically cultivated in a cell incubator at about 37° C. The incubator atmosphere should be humidified and should contain about 3-10% carbon dioxide in air, more preferably about 8-10% carbon dioxide in air and most preferably about 8% carbon dioxide in air, although cultivation of certain cell lines may require as much as 20% carbon dioxide in air for optimal results. Culture medium pH should generally be in the range of about 6.2-7.8, preferably about 7.1-7.4, and most preferably about 7.1-7.3. The cells may be cultured under different conditions (pH, temperature and/or carbon dioxide) to enhance protein production.

Cells in closed or batch culture should undergo complete medium exchange (i. e., replacing spent media with fresh media) when the cells reach a density of about $1.5-2.0\times10^6$ cells/ml. Cells in perfusion culture (e. g., in bioreactors or fermenters) will receive fresh media on a continuously recirculating basis.

Virus Production

In addition to cultivation of cells in suspension or in monolayer cultures, the present media may be used in methods for producing viruses from mammalian cells. Such methods comprise (a) contacting a cell (e.g., a mammalian cell) with a virus under conditions suitable to promote the infection of the cell by the virus; and (b) cultivating the cell in the culture media described herein under conditions suitable to promote the production of virus by the cell. The cell may be contacted with the virus either prior to, during or following cultivation of the cell in the culture media. Optimal methods for infecting a mammalian cell with a virus are well-known in the art and will be familiar to one of ordinary skill. Virus-infected mammalian cells cultivated in the culture media described herein may be expected to produce higher virus titers (e. g., 2-, 3-, 5-, 10-, 20-, 25-, 50-, 100-, 250-, 500-, or 1000-fold higher titers) than cells cultivated in a cell culture media other than the cell culture media described herein.

These methods may be used to produce a variety of mammalian viruses and viral vectors, including but not limited to adenoviruses, adeno-associated viruses, retroviruses and the like, and are most preferably used to produce adenoviruses or adeno-associated viruses. Following cultivation of the infected cells in the culture media described herein, the used culture media comprising viruses, viral vectors, viral particles or components thereof (proteins and/or nucleic acids (DNA and/or RNA)) may be used for a variety of purposes, including vaccine production, production of viral vectors for use in cell transfection or gene therapy, infection of animals or cell cultures, study of viral proteins and/or nucleic acids and the like. Alternatively, viruses, viral vectors, viral particles or components thereof may optionally be isolated from the used culture medium according to techniques for protein and/or nucleic acid isolation that will be familiar to one of ordinary skill in the art.

Recombinant Protein Production

The compositions and methods described in the instant disclosure may be use to make cell culture media, which in turn may be used for the production of recombinant products such as peptide and/or proteins from the recombinant cells. Cells include eukaryotic cells, which may be grown in suspension. Preferably, the recombinant cells are mammalian cells, and particularly, the mammalian cells are grown in suspension. Accordingly, the compositions and methods described here, and the media produced thereof, are useful for cultivating a cell (e.g., a mammalian cell) that has been genetically engineered to produce a polypeptide in the culture media prepared using the compositions and methods described here. Optimal methods for genetically engineering a mammalian cell to express a polypeptide of interest are well-known in the art and will therefore be familiar to one of ordinary skill. Cells may be genetically engineered prior to cultivation in the media of the disclosure, or they may be transfected with one or more exogenous nucleic acid molecules after being placed into culture in the media. Genetically engineered cells may be cultivated in the present culture media either as monolayer cultures, or more preferably, as suspension cultures. Following cultivation of the cells, the polypeptide of interest may optionally be purified from the cells, and/or the used culture medium according to techniques for protein isolation that will be familiar to one of ordinary skill in the art.

Example 1: Ethanolamine Degradation in the Presence of Amino Acids

It was observed that ethanolamine was stable in the presence of glucose alone but was rapidly labile, especially at elevated temperatures (for e.g., >30° C.) in the presence of the combination of glucose and amino acids. Three dry powder cell culture media samples were tested. The first contained ethanolamine and glucose but no amino acids. The second contained ethanolamine, glucose, and a combination of amino acids. The third contained ethanolamine, glucose, amino acids and, additionally, choline chloride, calcium nitrate.4H2O and sodium phosphate dibasic. Samples were stored at 0° C. and 37° C. for 7 days and then reconstituted with water for injection (WFI), filtered through 0.22μ filters, and analyzed by HPLC to measure the concentration of ethanolamine (mg/L). As shown in Table 1, the dry media containing ethanolamine and glucose (without amino acids) exhibited a small decrease in ethanolamine from 0° C. to 37° C. (about 3%), whereas the addition of amino acids to the dry media results in a decrease in ethanolamine of about 90%.

TABLE 1

Rapid Degradation of Ethanolamine in Presence of Amino Acids

| Test Samples | 0° C. (mg/L) | 37° C. (mg/L) | % Difference (0° C. to 37° C.) |
|---|---|---|---|
| Ethanolamine and Glucose | 66.192 | 64.297 | 2.86% |
| Ethanolamine, Glucose, and Amino Acids | 70.824 | 9.895 | 86.03% |
| Ethanolamine, Glucose, and Amino Acids+++ | 69.870 | 7.107 | 89.83% |

Example 2: Cell Culture Potency of Ethanolamine Derivatives

We tested a range of ethanolamine derivatives for cell culture potency, including phosphorylethanolamine (PE), triethanolamine (TE), diethanolamine (DE), monomethyl-ethanolamine (MME), dimethylethanolamine (DME), and N-acetylethanolaine (NAE). Initially, we tested all compounds at a molar equivalent of ethanolamine and did not see any derivatives that supported cell growth at comparable levels to ethanolamine. The cell line used was DG44-EPO, a CHO cell line expressing recombinant erythropoietin, that requires ethanolamine for good growth. Cells were inoculated at 3×105/ml and cultured bi-weekly for 3 subpassages in each condition prior to starting the assay. The assay was also inoculated at 3×105/ml but followed for 8 days for viable cell density from a ViCell cell counter.

Figure 1B:
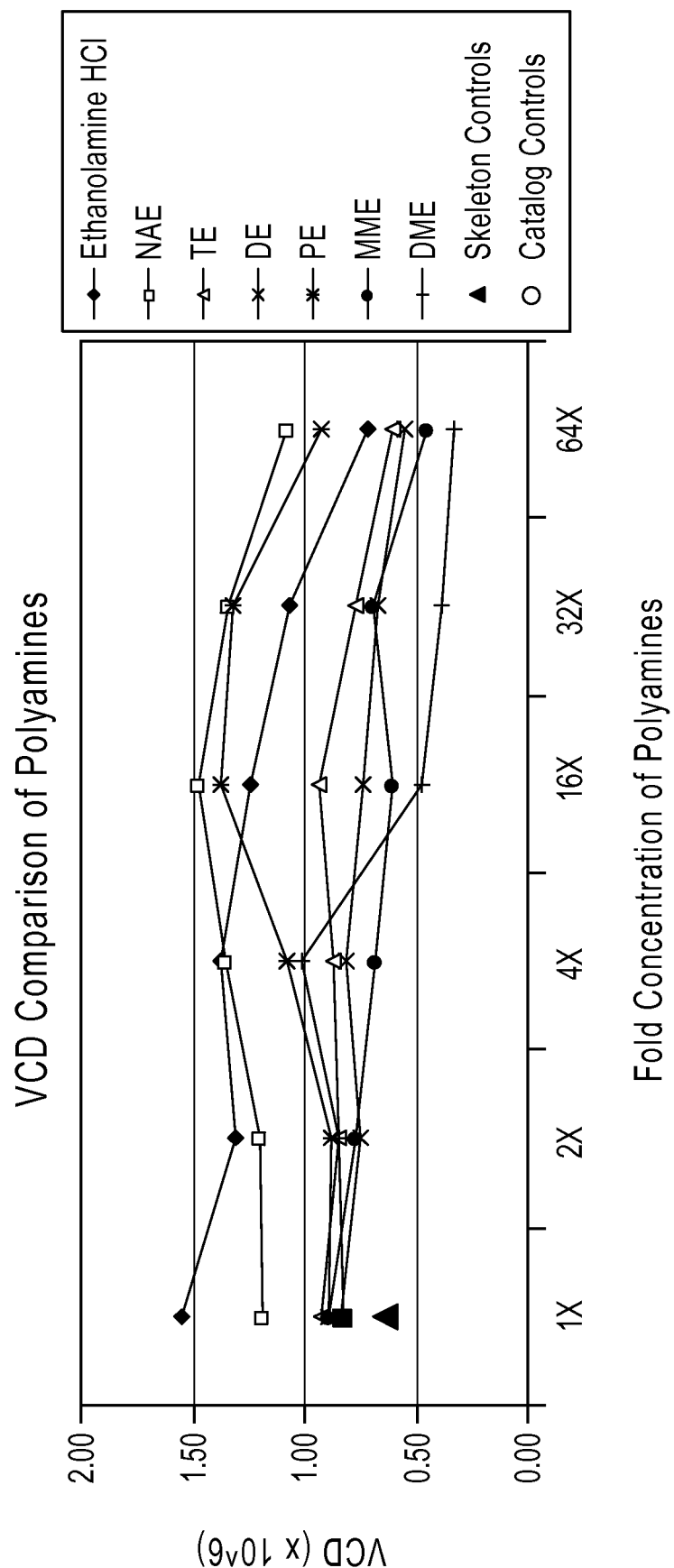

Next we titered the compounds up to 64× of a molar equivalent. Both phoshorylethanolamine and NAE at about 16× the molar equivalent yielded similar growth potential to ethanolamine. See FIGS. 1A and 1B. In another set of experiments, NAE at about 16× the ethanolamine molar equivalent was again shown to be able to supplement an ethanolamine-sensitive line as well as ethanolamine. These latter experiments were performed in 24 well culture trays. Cells were inoculated at 1×105/ml and samples harvested at day 12. Because the nitrogen atom in NAE is contained within an amide structure, it is expected that NAE should be stable and can be used in place of ethanolamine in cell culture media.

Figure 2A:
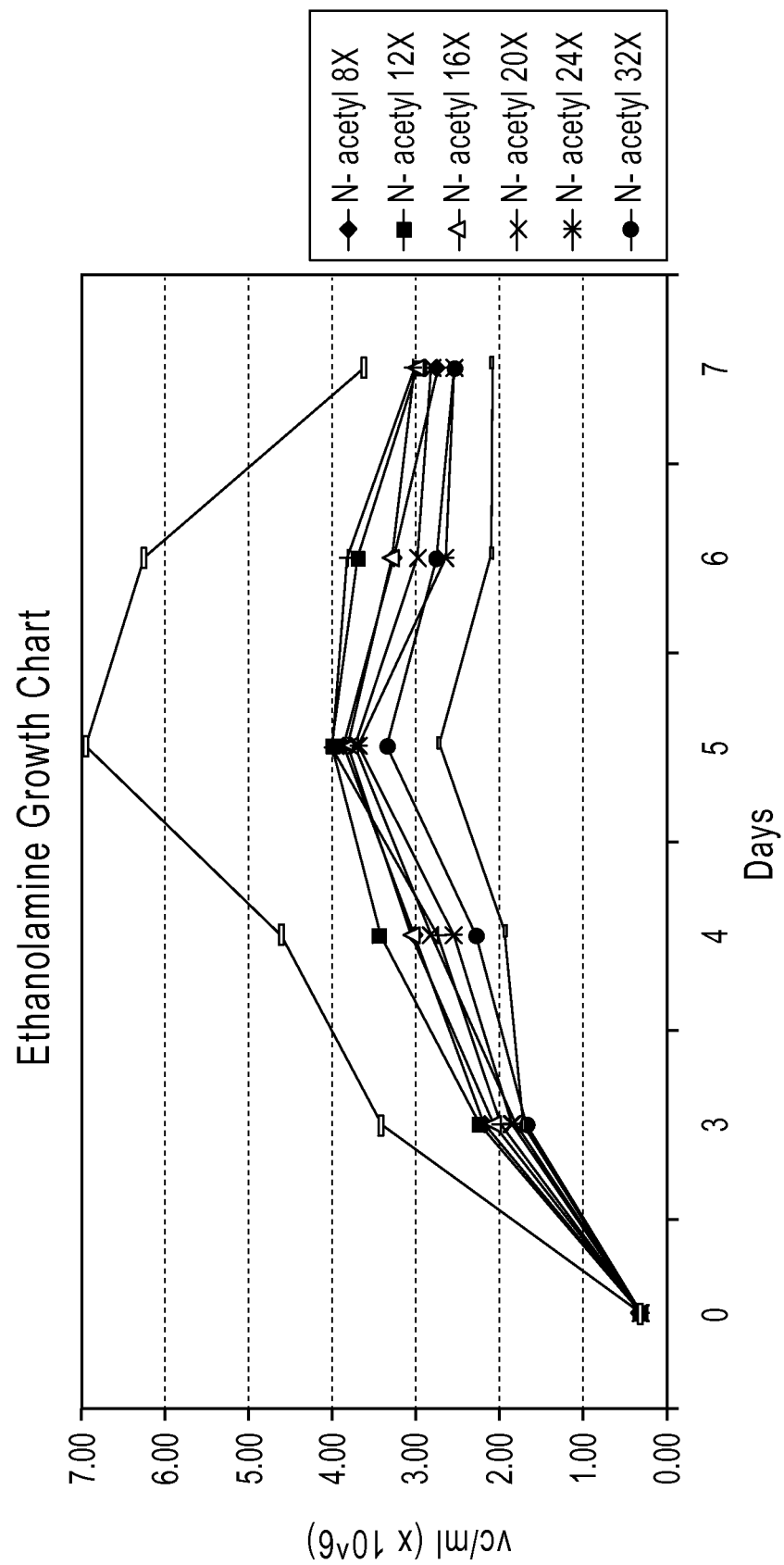
FIG. 2A shows a cell growth titration assay in which N-acetylethanolaine (NAE), a derivatized ethanolamine, at about 16-20× the ethanolamine molar equivalent, was able to supplement an ethanolamine-sensitive line comparable to ethanolamine
Figure 2B:
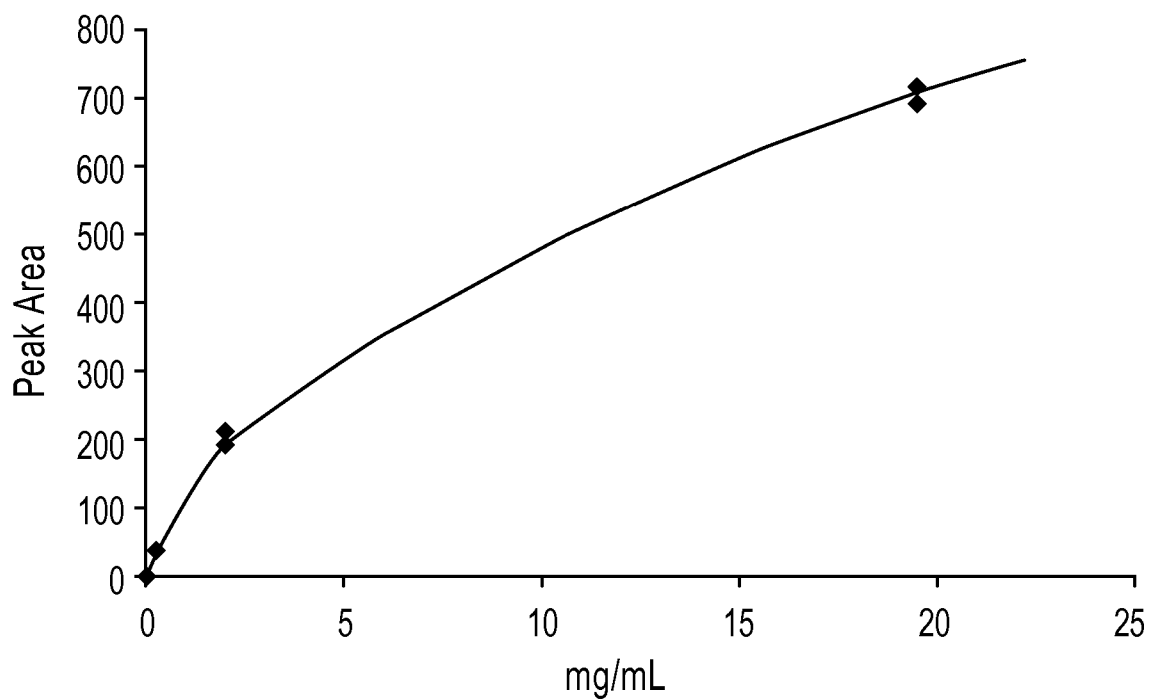
FIG. 2B shows that N-acetylethanolaine (NAE) can be measured by LC-mass spectrometry in any given sample, say, a cell culture medium. The graph shows the concentration curve for analytical grade pure NAE detection by LC-Mass Spectrometry.
Figure 4A:
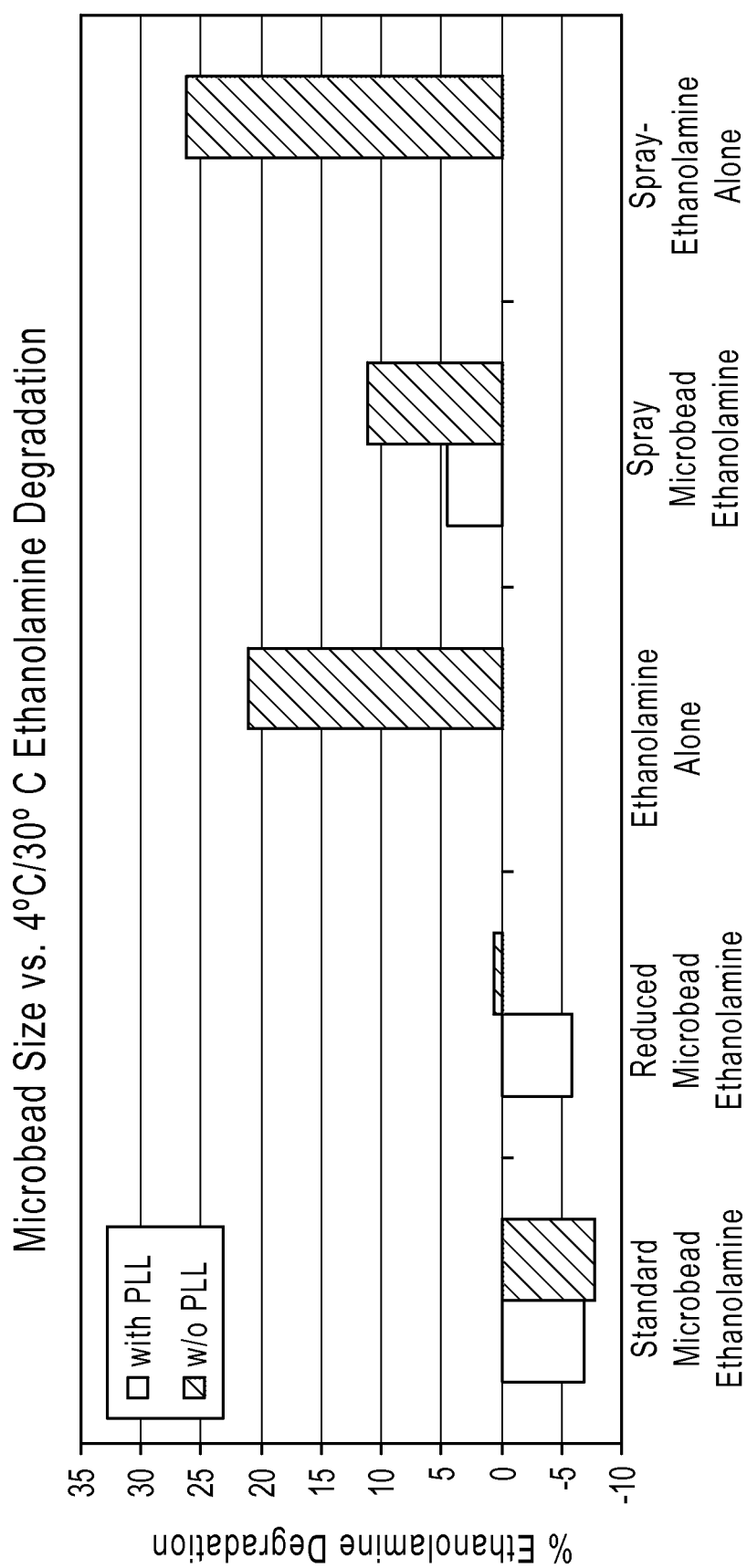
FIG. 4A: Further refinement of optimal bead size was determined. Accelerated shelf life stability studies of encapsulated ethanolamine (within 2% alginate microbeads) were performed on day 7. Results (% degradation) are shown of capsules that were either coated, or not coated, with PLL. Microencapsulation of ethanolamine with alginate beads showed markedly less degradation of ethanolamine compared to controls with ethanolamine alone, and even less degradation (degradation brought down to 0) when beads were PLL coated, in the extended shelf life stability studies (7 days), at temperatures 4° C. and 30° C. Protection with smaller beads (spray-dried) was less desirable compared to the standard and reduced microbeads. Results show that microencapsulation may protect ethanolamine.
Figure 4B:
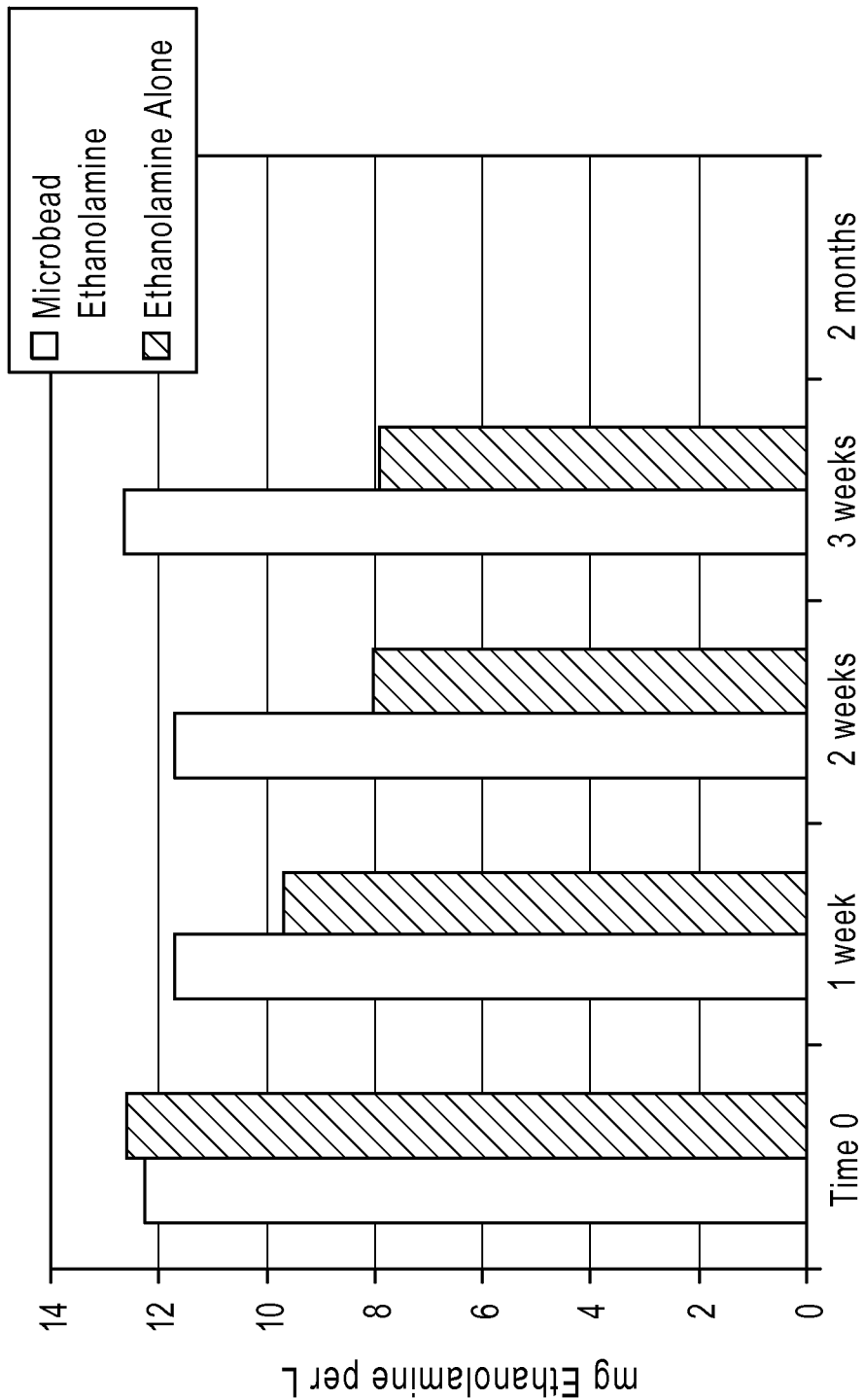
FIG. 4B: Stability studies showed that microencapsulation protected ethanolamine at room temperature, for more than 3 weeks, up to two months was tested.
Figure 4C:
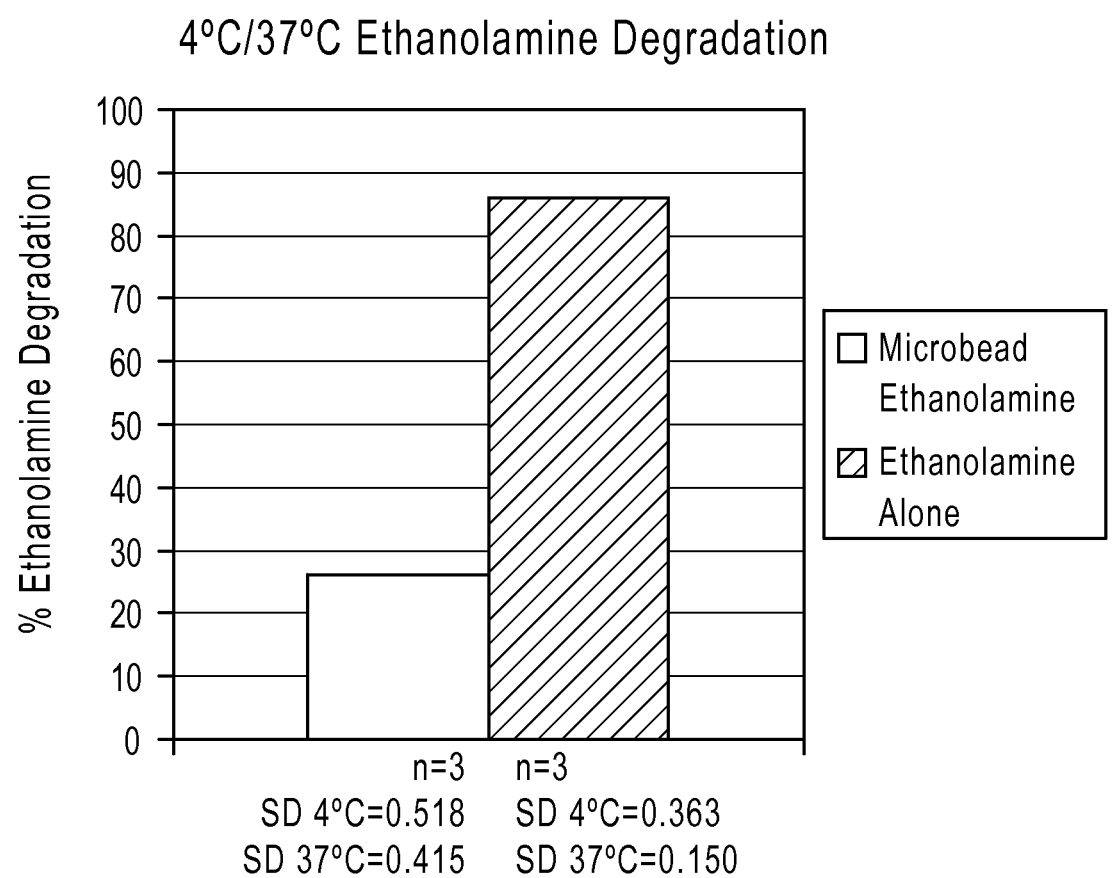
FIG. 4C: Further testing was done to confirm microencapsulation of ethanolamine. Accelerated shelf life studies showed stability of ethanolamine within 2% alginate microbeads, observed up to 7 days. Control ethanolamine was mixed with proline. These results suggest that microencapsulation of labile compounds such as ethanolamine can improve shelf-life and reduce shipping costs. Currently certain dry media formulations such as AGT™ are shipped on dry ice internationally, or by refrigeration within the US. Improved storage and handling conditions can reduce packaging waste (green packaging) and reducing shipping costs (less weight–green technology).
Figure 5:
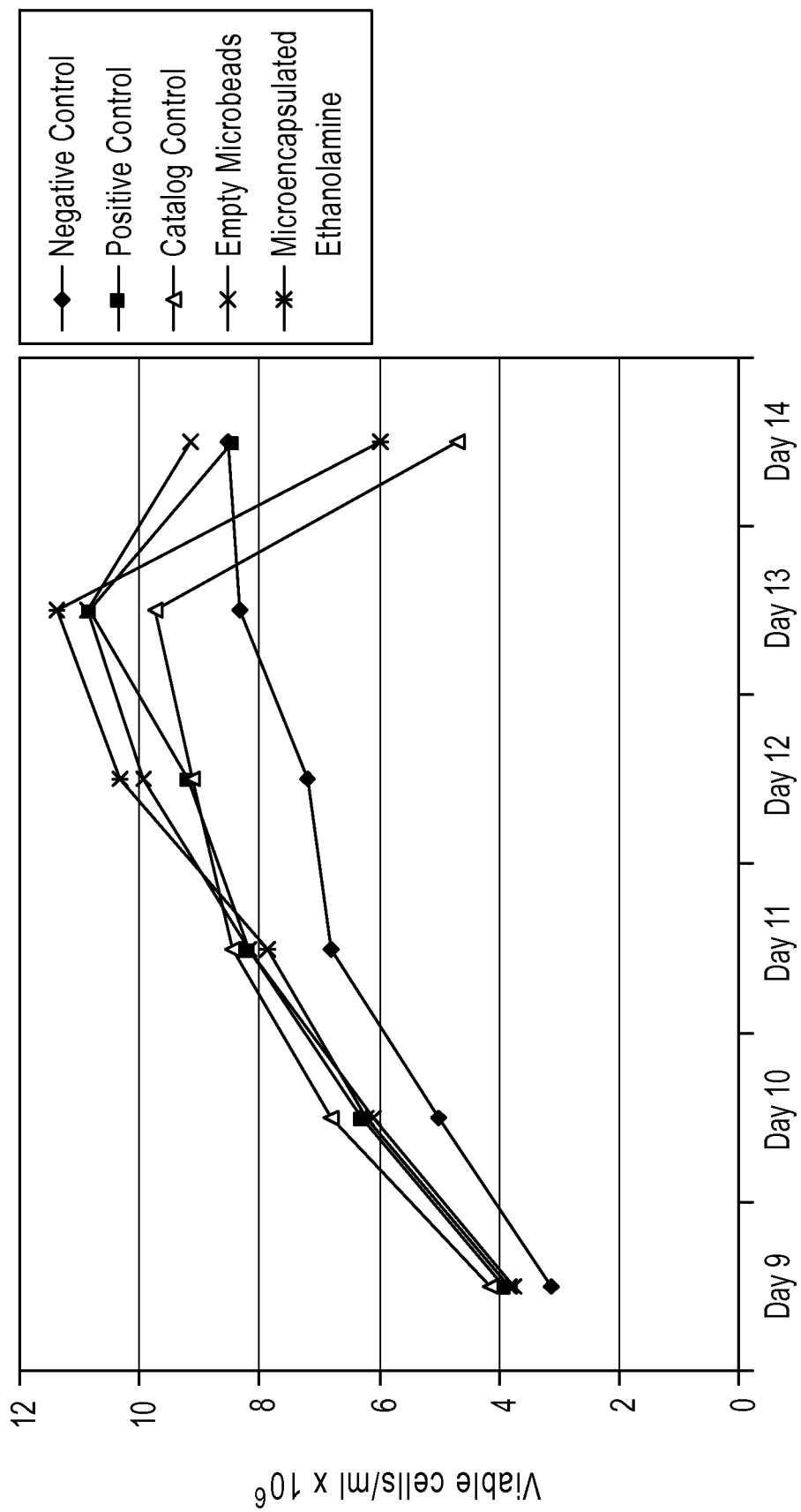
FIG. 5 shows that DG44-EPO cell growth is fully supported by microencapsulated ethanolamine. Empty microbeads did not inhibit cell growth. Further, microencapsulated ethanolamine did not inhibit cell growth, as seen with recombinant CHO-DG44 cells expressing EPO protein.

In FIG. 2A, the data shows that N-acetylethanolamine (NAE) can perform in a cell growth assay comparable to ethanolamine, although at a higher concentration (8-12-fold). At this time, a molar equivalent of NAE may not provide the same growth performance as for ethanolamine. Nevertheless, NAE may be used in certain new formulations, because conditions without ethanolamine showed lower growth. FIG. 2B shows a detection assay for NAE by LC-MS, whereby NAE can be detected in any formulation, including media formulations. The LC-MS chromatogram shows that the standard sample of N-acetylethanolamine using analytical grade NAE to detect NAE concentration variations. The negative control is without ethanolamine. The line way above the rest should be disregarded—it is a CD CHO catalogue control, not relevant to this assay.

FIG. 2B: Detection assay for N-acetyl ethanolamine using analytical grade NAE. Detection of NAE is between 19-20,000 μg/ml, well within media concentration ranges.

Example 3: Ethanolamine/Glucose Complex

One way to reduce ethanolamine degradation in a dry powder cell culture medium is to form a complex between ethanolamine and a sugar, such as glucose. To form the complex or a crystalline paste, ethanolamine is dissolved in WFI at a specified amount and then added over a given weight of glucose. Immediately a spatula is used to knead the ethanolamine-glucose-WFI mixture until it forms a paste consistency. The pasty mixture is then spread flat and dried overnight under a hood followed by final drying in a dessicator. The dried mixture is Fitzmilled at sizing specifications and blended with the dry powder cell culture medium. An exemplary protocol for complexing ethanolamine with glucose is as follows:

1) For a 2000 g lot of Advanced Granulation Technology—AGT™ cell culture medium (Invitrogen, Carlsbad, Calif.), using 5% w/w of crystalline entity to total AGT™ weight: 100 g glucose to use to form crystalline entity (deduct 100 g from remaining glucose in the AGT™ (Invitrogen, Carlsbad, Calif.) process).
2) Calculate the amount of WFI to make crystalline entity, using 8 ml of WFI for each 15 g of glucose. Therefore 53.33 ml of WFI is used for 100 g of glucose.
3) Add 2.086 g of ethanolamine to the WFI prior to making the crystalline entity and stir to dissolve, pH to about 7.0.
4) To make the crystalline entity:
   a. Place the glucose in a flat, non-reactive pan with low sides;
   b. Add entire WFI-ethanolamine solution;
   c. Quickly use a metal spatula to knead, ladle, or paddle mash the liquid into the glucose. Continue mixing and mashing for several minutes. The glucose mix will change in consistency from a gritty powder into a smooth, putty-like state as the glucose changes physical form. Continue mixing and kneading until the mixture is homogenous. Then spread the homogenous mixture into a thin layer and chop into smaller pieces with the spatula and place overnight under a fume hood in the dark or with subdued lighting.
   d. After about 12 hours, collect the crystalline entity and use AGT™ (Invitrogen, Carlsbad, Calif.) sizing parameters (e.g., Fitzmill at 1000 rpm, forward knives, 0.050" screen) to break up.

5) Blend crystalline entity into AGT™ (Invitrogen, Carlsbad, Calif.) bulk after the granulation stage.

One way of rapidly estimating shelf life is by performing an accelerated shelf life study. One way to perform an accelerated shelf life study is to incubate the test material at both lowered and elevated temperatures for a shortened period of time, such as 7 days. The stability of the ingredient of interest is determined by measuring the concentration of the ingredient after 7 days at both the lowered and elevated temperatures and calculating the % difference in the concentration of the ingredient.

Using the methodology described above, samples were prepared to measure the effect of glucose crystallization on ethanolamine stability in two different commercially available AGT™ (Invitrogen, Carlsbad, Calif.) cell culture media, EfficientFeed™ A (Invitrogen, Carlsbad, Calif.) and EfficientFeed™ C (Invitrogen, Carlsbad, Calif.), both of which contain amino acids. See Tables 2 and 3. Test samples containing ethanolamine were prepared and added to AGT™ (Invitrogen, Carlsbad, Calif.) bulk cell culture media. The ethanolamine-containing test samples included at least 1) ethanolamine complexed with glucose 2) dry grind ethanolamine and glucose (ethanolamine not complexed with glucose) and 3) dry grind ethanolamine with proline, as a positive control. After adding the test samples to the AGT bulk media, samples were incubated at 4° C., room temperature, and 30° C. for 7 days. Following the incubation, samples were reconstituted with WFI and the concentrations of ethanolamine (mg/L) were measured using HPLC, as described above. With both cell culture media, complexing ethanolamine with glucose reduced the degradation of ethanolamine (smaller % difference as compared to control sample). See Tables 2 and 3 below. In ongoing results, the glucose crystallization method was has so far shown 9m shelf life.

TABLE 2

Use of Glucose to Stabilize Ethanolamine (Media # 1)

| Test Samples | 4° C. (mg/L) | RT (mg/L) | 30° C. (mg/L) | % Difference (4° C. to RT) | % Difference (RT to 30° C.) |
|---|---|---|---|---|---|
| Ethanolamine complexed with glucose | 74.596 | 73.402 | 54.088 | 1.60% | 27.50% |
| Dry grind ethanolamine and glucose | 82.392 | 64.864 | 43.456 | 21.30% | 47.30% |
| Dry grind ethanolamine with proline | 84.617 | 68.465 | 47.815 | 19.20% | 43.50% |
| EfficentFeed ™ A (Invitrogen, Carlsbad, CA) and glucose | 27.969 | 26.032 | 18.609 | 6.90% | 33.50% |

TABLE 3

Use of Glucose to Stabilize Ethanolamine (Media # 2)

| Test Samples | 4° C. (mg/L) | RT (mg/L) | 30° C. (mg/L) | % Difference (4° C. to RT) | % Difference (RT to 30° C.) |
|---|---|---|---|---|---|
| Ethanolamine complexed with glucose crystal | 46.176 | 39.591 | 34.285 | 14.30% | 25.80% |
| Ethanolamine and polyamine complexed with glucose crystal | 40.519 | 38.097 | 31.280 | 6.00% | 22.80% |
| Dry grind ethanolamine with proline and glucose | 55.873 | 39.581 | 25.002 | 29.20% | 55.30% |

Example 4: Sequestering Ethanolamine in Alginate Microcapsules

Microencapsulation provides another mechanism of physically separating or sequestering or protecting ethanolamine from amino acids, particularly in powdered cell culture media. By way of example, alginate can be used for microencapsulation.

To prepare alginate-ethanolamine microcapsules, ethanolamine was dissolved in 2% alginate solution in water (WFI), degassed, and added dropwise using a needle or syringe, or by aerosol spraying (forming a spray mist) into a calcium bath (13.32 g/L calcium chloride), where the alginate is cross-linked by the calcium to form a hydrogel. A "1000×" concentration of beads was used, meaning that 1 ml of alginate solution contains the amount of ethanolamine in 1000 ml of medium (i.e., 0.068 g ethanolamine in say 1 L of Efficient FeedA). Ethanolamine becomes trapped within the alginate hydrogel to form tiny beads or microcapsules. Next the ethanolamine-containing beads or microcapsules were dried, by placing them under an airflow overnight and then placing them within a dessicator with CaSO4 underneath the shelf with a vacuum applied for several hours. Depending on the method of microcapsule formation (droplet vs mist spraying), the process produces a fractile, hard, smaller spherical bead that can directly be mixed with any dry powder media including AGT or APM media.

In certain instances, poly-L-lysine was added to enhance ethanolamine stabilization. A poly-1-lysine (PLL) coating was added to the microcapsules using the technique in Breguet et al., Cytotechnology, 2007, 53:81-93. Briefly, 1 ml of 0.15% PLL is added to each beaker of 1 L-equivalent of beads, incubated for ~15 minutes with occasional swirling to ensure that all the beads are coated. After 15 minutes, excess PLL is aspirated off with a pipette. Beads are dried and dessicated as described before.

After adding the ethanolamine-containing alginate microcapsules to, say, the AGT bulk media, samples were incubated at 4° C., room temperature, and 30° C. for 7 days. Following the incubation, samples were reconstituted with WFI and the concentrations of ethanolamine (mg/L) were measured using HPLC, as described above. The data in Table 4 shows significantly less degradation of ethanolamine when complexed with alginate microcapsules as compared to a control sample containing ethanolamine with proline, an amino acid that has been used as a dispersant for minor components (in this case ethanolamine). Also see FIGS. 3A-B, 4A-B and FIG. 5.

TABLE 4

Use of Alginate Microcapsule to Stabilize Ethanolamine

| Test Samples | 4° C. (mg/L) | RT (mg/L) | 30° C. (mg/L) | % Difference (4° C. to RT) | % Difference (RT to 30° C.) |
|---|---|---|---|---|---|
| Ethanolamine complexed with alginate | 62.521 | 57.999 | 48.666 | 7.2% | 22% |
| Pre- grind ethanolamine with proline | 52.552 | 42.033 | 29.033 | 20% | 45% |

After adding the microcapsules (with or without PLL) to the AGT™ (Invitrogen, Carlsbad, Calif.) bulk media, samples were incubated at 4° C., room temperature, and 30° C. for 7 days. Following the incubation, samples were reconstituted with WFI and the concentrations of ethanolamine (mg/L) were measured using HPLC, as described above. The data in Table 5 show that coating alginate microcapsules with PLL prevented ethanolamine degradation. See FIGS. 3A-3B and FIGS. 4A and 4B.

TABLE 5

Use of Poly-L-Lysine to Enhance Ethanolamine Stabilization

| Test Samples | 4° C. (mg/L) | 30° C. (mg/L) | % Difference (4° C. to 30° C.) |
|---|---|---|---|
| Ethanolamine/alginate microcapsule (with PLL) | 59.570 | 61.881 | -3.7% |
| Ethanolamine/alginate microcapsule (w/out PLL) | 62.014 | 54.724 | 11.8% |
| Pre- grind ethanolamine with proline | 60.496 | 42.031 | 30.5% |

Example 5: Encapsulation of a Dendrimer-Susceptible Test Compound Complex

In one example, a sequestering agent like alginate was used to encapsulate or embed a dendrimer-ethanolamine complex. Dendrimers are hyper-branched synthetic macromolecules that can be made using controlled sequential processes to give them defined structural and molecular weight characteristics. They are reported to be useful not only to protect sensitive substances, but mainly for improving on timed release of embedded components within a given medium. Further, when cell recognition or cell attachment moieties are incorporated into dendrimers, the dendrimer may specifically attach to a cell and deliver its contents. This is highly useful in targeted delivery of a valuable substance, or an extremely labile substance, or highly sensitive cell regulatory molecules. This study was done to see if microencapsulation of a dendrimer-labile molecule complex stabilizes the molecule from degradation, and further, whether the labile substance can be stored for long periods of time under ambient conditions like room temperature while associated with a dendrimer in the dry state. The procedure for forming dendrimers was done as described in Astruc et al., Chem. Rev. 2010, 110:1857-1959, which is hereby incorporated by reference in its entirety. Briefly, different types of dendrimers can be synthesized based on the core structure that initiates the polymerization process. The microencapsulated dendrimers of this disclosure are described in FIG. 6. In one embodiment, the dendrimer was encapsulated in a capsule of alginate. Alginate protects the dendrimers and upon reconstitution, releases the dendrimers with the sensitive substance. Alginate is retained on the membrane filter during filtration. The exposed dendrimer can target the sensitive substance to a cell due to the presence of cell recognition sites present on the dendrimer, thereby improving availability of sensitive or low-concentration substances such as growth factors like insulin, vitamins, etc. to the cell. The results are shown in FIGS. 6, 7a, 7b, 8, 9 and 10.

Figure 8:
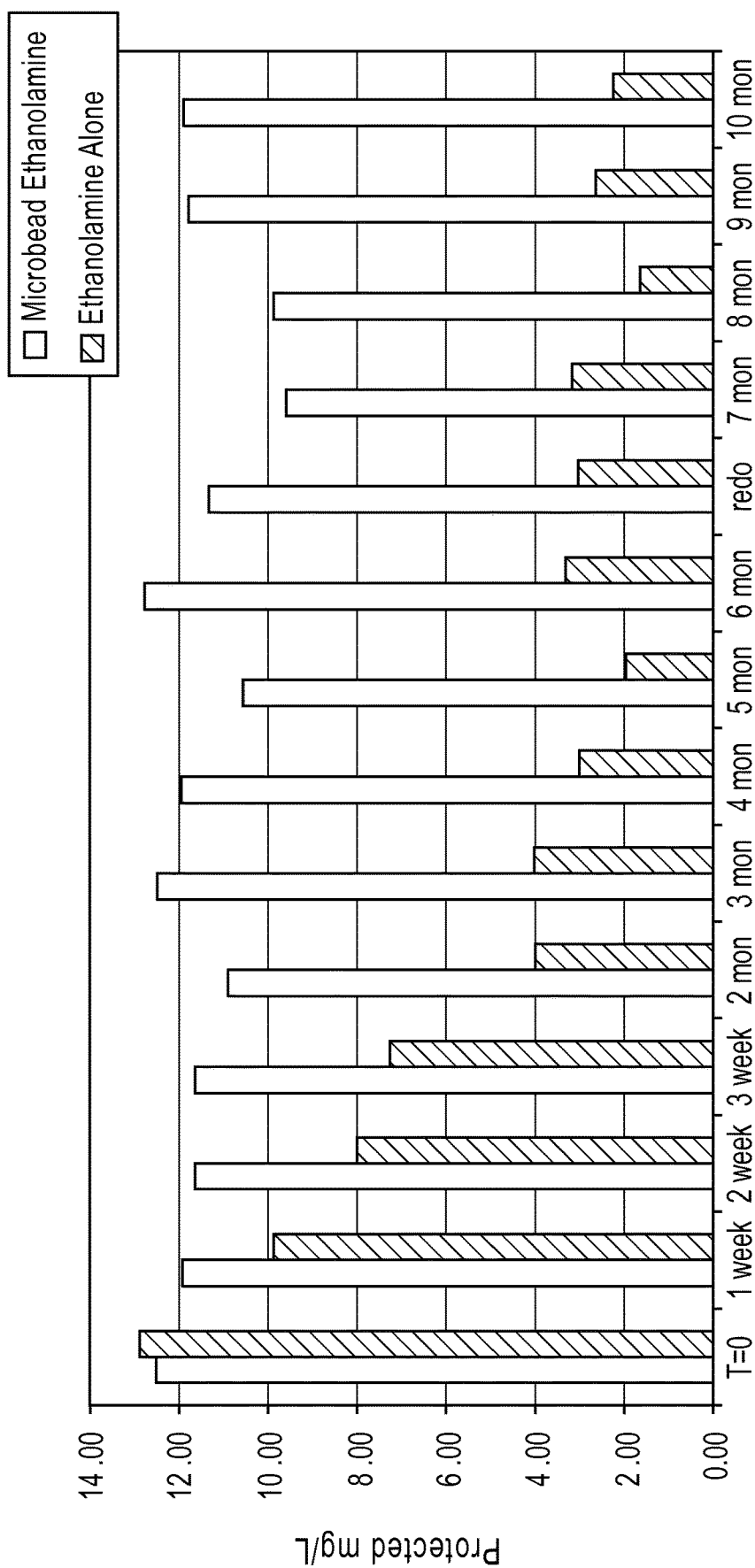
FIG. 8: Microbeads protection studies during real-time ambient storage. Unencapsulated ethanolamine activity drops quickly in AGT™media under ambient conditions, but remains potent for many months longer when microencapsulated.

In FIG. 8, the unprotected ethanolamine potency dropped quickly in AGT™ under ambient conditions while maintaining potency for many months longer when protected by microencapsulation (microbeads). Microencapsulated ethanolamine continued to show no change in potency even up to ten months and beyond at ambient temperatures (see FIG. 8).

Further examples for microencapsulating labile compounds other than ethanolamine are shown below. A sequestering agent like alginate was used to encapsulate or embed a dendrimer-insulin complex. The labile compound insulin was polymerized with PAMAM dendrimer, and further microencapsulated in alginate microbeads with or without PLL. Briefly, for dendrimer generation, PAMAM 2.5 (carboxylate surface groups) was used. Insulin was conjugated onto the dendrimer to which RGD sequences were also added to target the cell surface. The ratios of components in this complex was dendrimer:RGD:insulin=1:7:12.

Protocol for Dendrimer Conjugation:

Concentration of conjugate and alginate was adjusted as on attachment. Next conjugate was added to the alginate and mixed several minutes to distribute evenly. It was dripped through a 26 gauge needle using a 1 ml syringe into a calcium chloride bath (13.32 g/L). It was left to incubate for 30 minutes to solidify microcapsules. Then rinsed 1× in a solution also containing the dendrimer conjugate to prevent loss of component from the microcapsules. Then dried overnight in a vacuum over desiccant. The loaded microbeads were then added to AGT dry-format medium or used by adding directly into a liquid medium.

Insulin-Dendrimer-RGD Dilution Protocol

The insulin concentration of the dendrimer-insulin-RGD conjugate was estimated to be ~2 mg/ml (pg 165/168). It needed to be diluted in half to get to ~1 mg/ml (1000 μg/ml).

Stock r-insulin for assays was set at 1000 μg/ml, which is a 100× of a 10 μg/ml concentration. This was equivalent to a 1000× of a 1 μg/ml concentration, which was well within the titerable insulin concentration with the 96-well assay (pg. 160). So the effective dilution of the insulin used for microencapsulation (a, pg 168) is 1:1000×. In addition, 1:1000 was what we set for the microencapsulation equivalency (1 ml of alginate beads was used for 1000 ml of medium). The Eugene conjugate control would also be diluted first 1:1 (above) and then used at 1:1000 dilution.

We needed to add the dendrimer-insulin-RGD conjugate (liquid) to 3% alginate so as to yield 2% alginate final. (1+0.5). This dilution did not impact the dendrimer-insulin-RGD conjugate amount since all the dendrimer added would go into the beads and ultimately into the specified medium. Example: 0.1 ml of dendrimer-insulin-RGD conjugate was used for 100 ml of final medium volume (at 1:1000). Added this 0.1 ml dendrimer-insulin-RGD to 0.2 ml of 3% alginate to equal 2% alginate. Used all of it by dripping into calcium bath and processing as on pg. 167 and adding to 100 ml medium. Similarly, the positive insulin control (b, pg. 168) was diluted to 1:1000× not to 10 μg/ml.

Figure 7A:
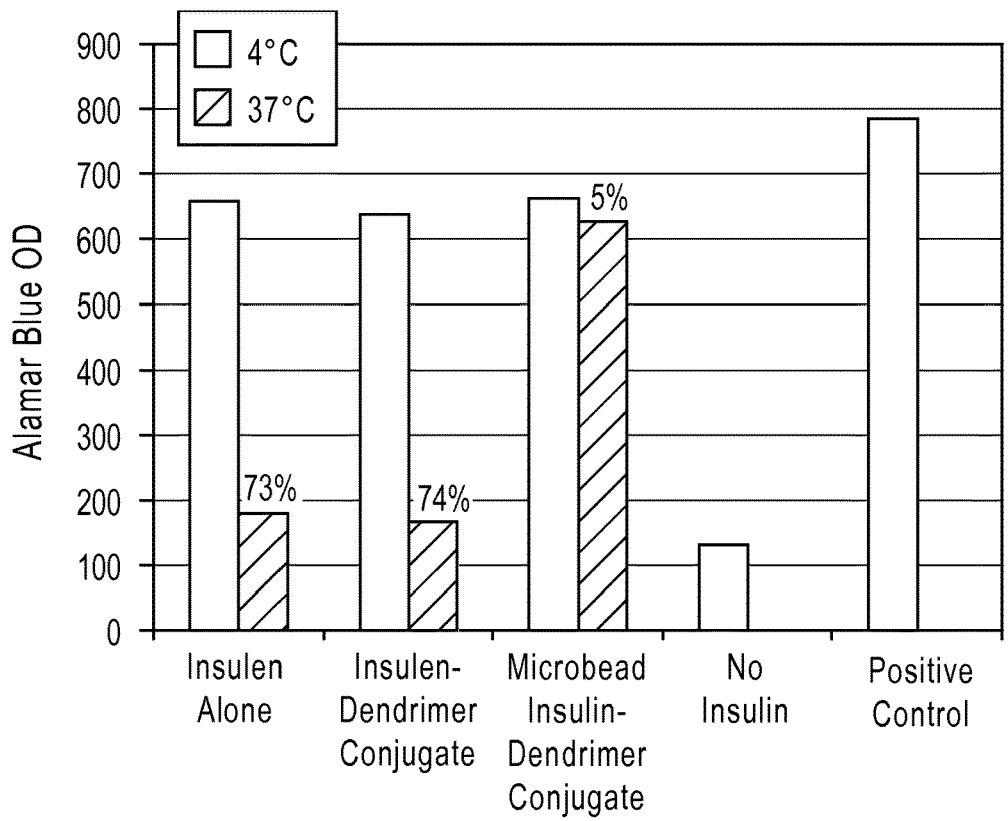
FIG. 7A: Microencapsulation of the dendrimer (containing test substance insulin) has substantially enhanced stability at room temperature compared to unencapsulated dendrimer (with insulin), or insulin alone. The potency of insulin in dendrimer is comparable to that of insulin alone at 4° C.
Figure 7B:
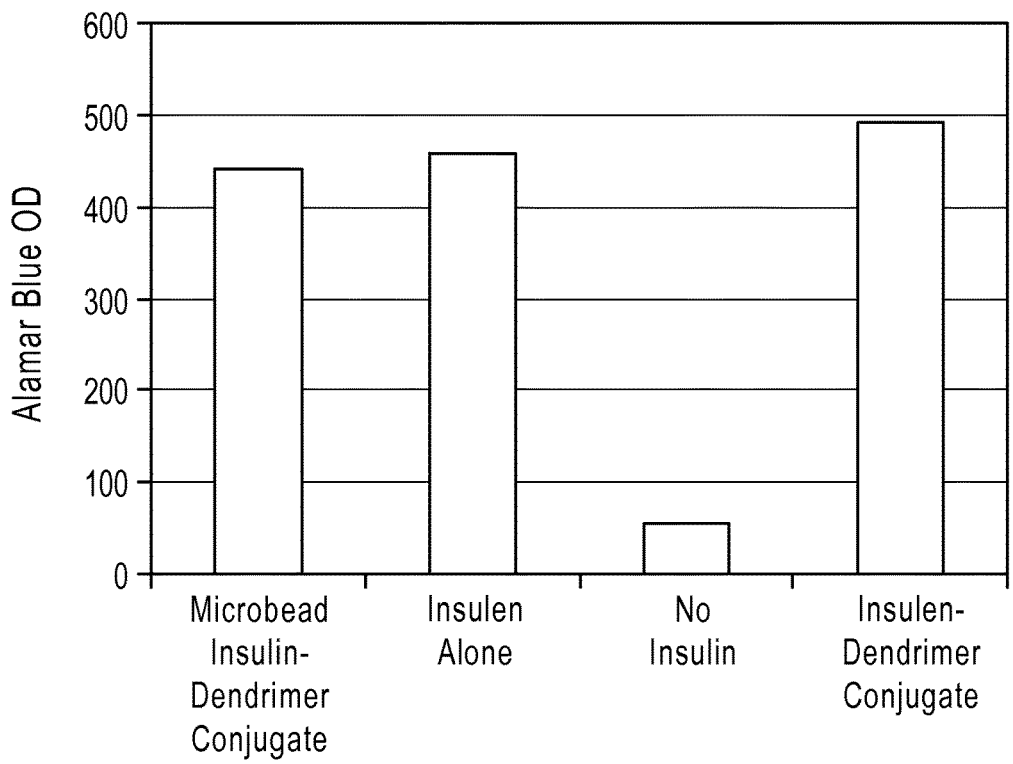
FIG. 7B: Impact of microencapsulation of the insulin-dendrimer-RGD covalent conjugate on the growth of HeLa cell Growth. Studies showed that all three conditions, the microencapsulated dendrimer bead (with insulin), unencapsulated dendrimer (with insulin), and insulin alone, all showed equivalent potency and growth characteristics of HeLa cells. Note: the microencapsulated dendrimer bead (with insulin) did not inhibit cell growth.
Figure 10:
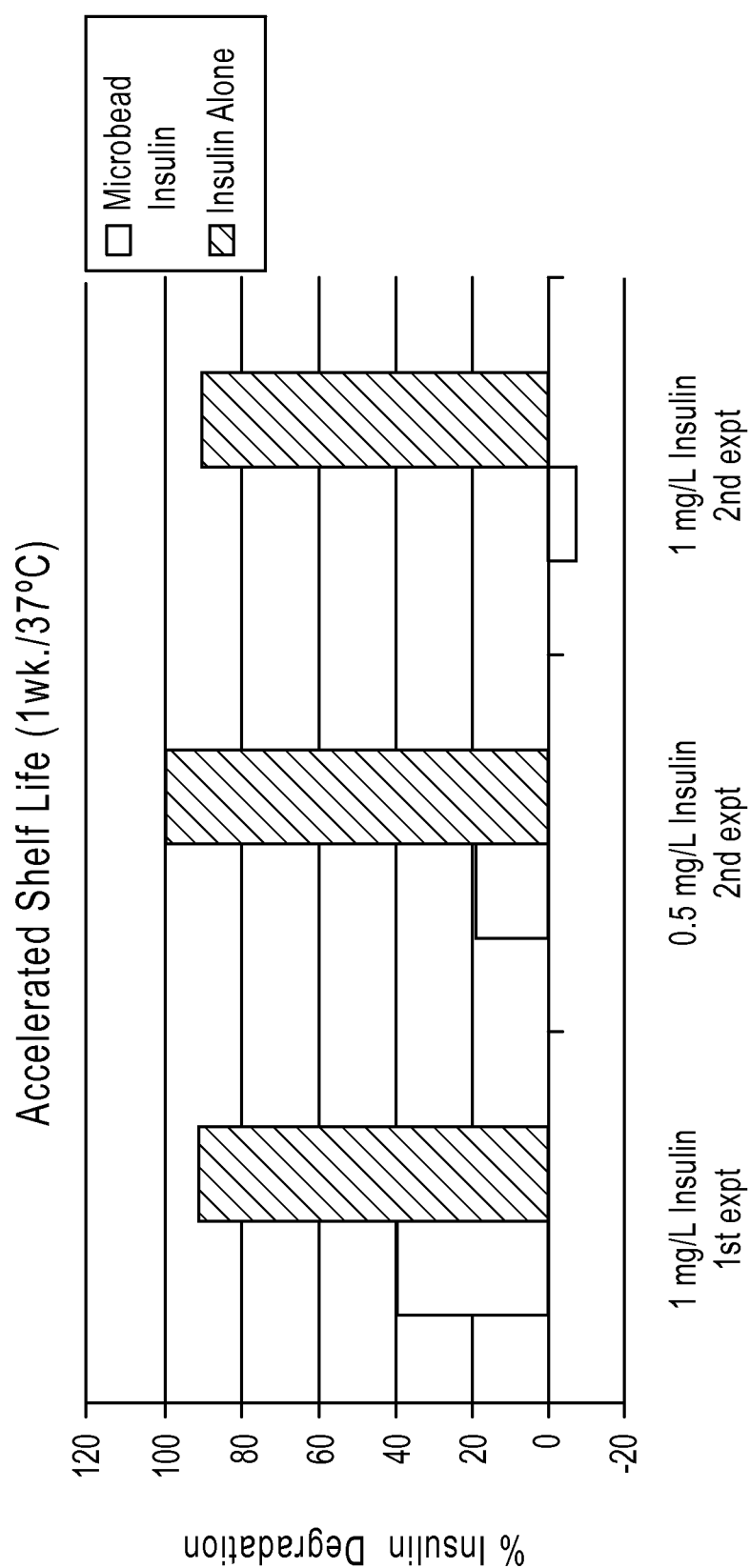
FIG. 10: Microencapsulation improved insulin stability. Therefore, there is potential for biomolecule protection in a dry-format medium.

As shown in FIG. 7A, microencapsulation of the dendrimer showed substantially enhanced stability at room temperature compared to the unencapsulated dendrimer with insulin, or with insulin alone (no dendrimer, no encapsulation with alginate). The potency of insulin in the dendrimer was comparable to that of insulin alone at 4° C. In addition, cell growth studies on the mammalian HeLa cell line with insulin alone (control), the dendrimer containing—microbeads (test), or microbeads without dendrimer all showed equivalent potency and growth characteristics of HeLa cells, and both the dendrimer or the alginate did not interfere with viability or growth of Hela cells, showing that the microencapsulation procedure was not toxic for cells (FIG. 7B). Accelerated shelf life studies showed that microencapsulation (microbead) improved insulin stability in dry format media for up to one week at 37° C. (FIG. 10).

Figure 9:
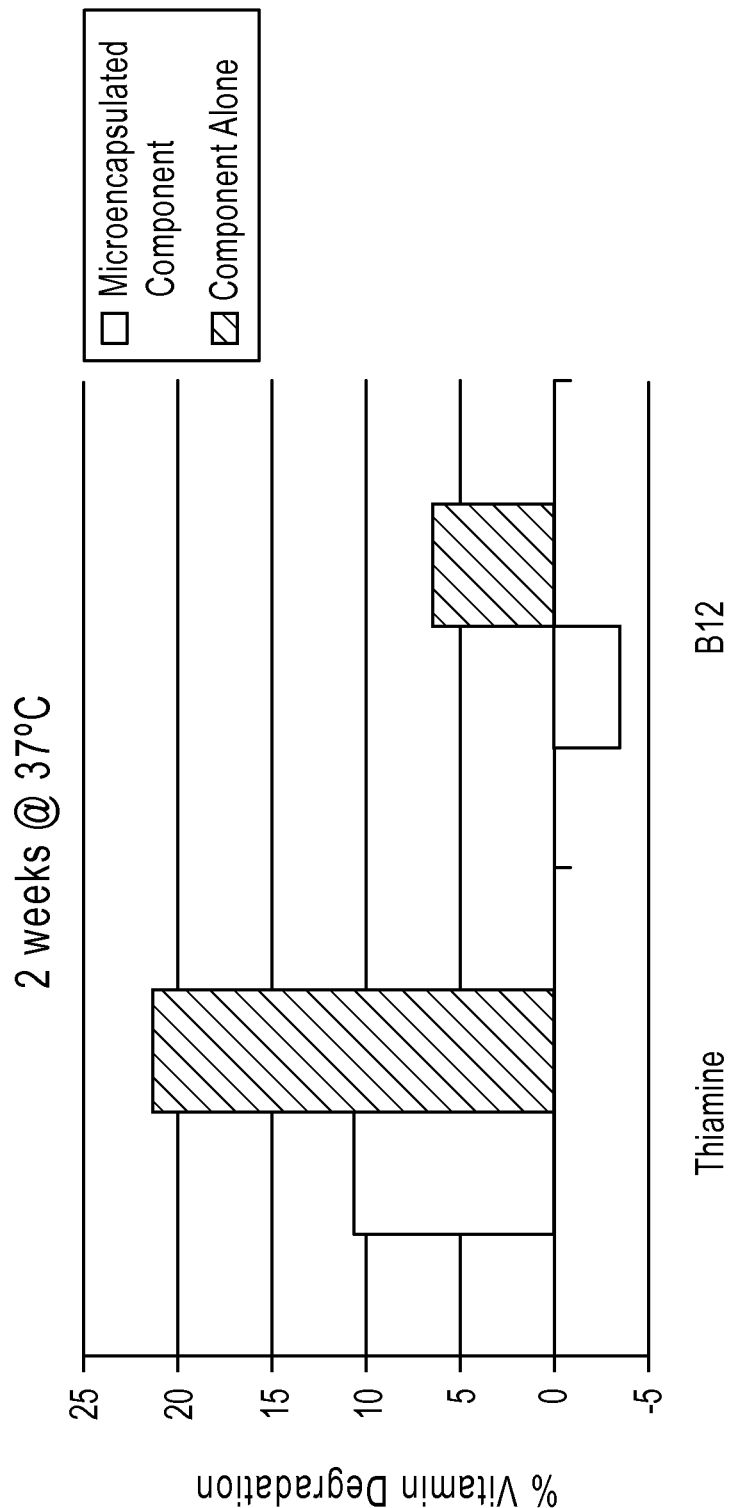
FIG. 9: Microencapsulation also improves vitamin stability.

In a further example, vitamins (for e.g., thiamine, vitamin B12, etc.) were used as test labile compounds for microencapsulation and addition to dry format media (FIG. 9). A sequestering agent like alginate was used to encapsulate or embed a dendrimer-vitamin complex, as described above for encapsulated insulin. As seen from FIG. 9, accelerated shelf life studies showed that microencapsulation greatly improved vitamin stability, for two weeks at 37° C.

Microencapsulation can extend storage conditions of sensitive compounds like ethanolamine, vitamins, growth factors, etc., which can positively impact shipping and handling of dry media formulations like AGT™, etc., at room temperature rather than at lower temperatures (for e.g., refrigeration or dry ice), which can decrease shipping costs. Microencapsulation of labile compounds in dry format media can therefore be viewed as a contribution to green technology, by the cheaper handling and storage of dry format cell culture media.

Unless otherwise defined, all technical and scientific terms used herein have the same meaning as commonly understood by one of ordinary skill in the art. In case of conflict, the present specification, including definitions, will control. It will be readily apparent to one of ordinary skill in the relevant arts that other suitable modifications and adaptations to the methods and applications described herein are obvious and may be made without departing from the scope of the disclosure or any embodiment thereof. In addition, the materials, methods, and examples are illustrative only and not intended to be limiting. All patents, patent applications, and published references cited herein are hereby incorporated by reference in their entirety.

What is claimed is:

1. A cell culture medium composition for culturing animal cells comprising: amino acids, vitamins, organic salts, inorganic salts, sugars and a protected labile molecule-dendrimer complex present in a dry powder format, wherein the protected labile molecule-dendrimer complex is protected by sequestration and is prevented from adverse reactions with another component in the cell culture medium composition, wherein the cell culture medium composition has enhanced stability and is capable of cultivating an animal cell in vitro under suitable conditions, wherein the protected labile molecule-dendrimer complex includes ethanolamine.

2. The cell culture medium composition according to claim 1 wherein the sequestration is by encapsulation of the labile molecule within a soluble matrix or an insoluble matrix.

3. The cell culture medium composition according to claim 2 wherein the soluble matrix or the insoluble matrix is further coated with a protective coating.

4. The cell culture medium composition according to claim 3 wherein the protective coating is poly-L-lysine or polyornithine.

5. The cell culture medium composition according to claim 2 wherein the soluble matrix is selected from the group consisting of a sugar, an alcohol, a ketone and an aldehyde.

6. The cell culture medium composition according to claim 5, wherein the soluble matrix sugar is a hexose sugar selected from the group consisting of glucose, mannose, fructose, maltodextrin and galactose.

7. The cell culture medium composition of claim 1, wherein the conditions produce a polypeptide, a virus, a virus-like particle or a vaccine.

8. The cell culture medium composition of claim 7, wherein the cell is a mammalian cell.

9. The cell culture medium composition of claim 8, wherein the mammalian cell is a Chinese Hamster Ovary (CHO) cell.

10. The cell culture medium composition of claim 1, wherein said cell culture composition is selected from the group consisting of a medium, a supplement, a feed and a media concentrate.

11. The cell culture medium composition of claim 1, wherein the labile molecule is reacted with a dendrimer to produce a dendrimer-labile molecule complex.

12. The cell culture medium composition of claim 11, wherein the dendrimer is selected from the group consisting of a polyamidoamine (PAMAM) dendrimer, a polypropyleneimine (PPI) dendrimer, a phosphorylated dendrimer, a polylysine dendrimer, a polyethylenimine dendrimer, an iptycene dendrimer, an aliphatic poly(ether) dendrimer, an aromatic polyether dendrimer, and a polypropylamine (POPAM) dendrimer.

13. The cell culture medium composition of claim 11, wherein the dendrimer-labile molecule complex is further encapsulated within a sequestering agent to form an encapsulated-dendrimer-labile molecule complex.

14. The cell culture medium composition of claim 13 wherein the sequestering agent is a soluble or an insoluble matrix.

15. The cell culture medium composition of claim 14, wherein the insoluble matrix is selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, poly-glycolic acid, PLGA (poly-lactic-co-glycolic acid), collagen, polyhydroxyalkanoates (PHA), poly-ε-caprolactone, poly-ortho esters, poly-anhydrides, polyphosphazenes, poly-amino acids, polydimethylsiloxane, polyurethanes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone and carrageenan.

16. The cell culture medium composition according to claim 14 wherein the soluble matrix is selected from the group consisting of a sugar, an alcohol, a ketone and an aldehyde.

17. The cell culture medium composition according to claim 16, wherein the soluble matrix sugar is a hexose sugar selected from the group consisting of glucose, mannose, fructose, maltodextrin and galactose.

18. The cell culture medium composition according to claim 13 wherein, the encapsulated-dendrimer-labile molecule complex is further coated with a protective coating.

19. The cell culture medium composition according to claim 18 wherein the protective coating is either poly-L-lysine or polyornithine.

* * * * *